United States Patent
Zhang et al.

(10) Patent No.: US 12,378,251 B2
(45) Date of Patent: Aug. 5, 2025

(54) TRIAZOLOPYRIMIDINE COMPOUND AND SALT, COMPOSITION AND USE THEREOF

(71) Applicant: SHANGHAI INSTITUTE OF MATERIA MEDICA, CHINESE ACADEMY OF SCIENCES, Shanghai (CN)

(72) Inventors: Ao Zhang, Shanghai (CN); Zehong Miao, Shanghai (CN); Chaodong Xiong, Shanghai (CN); Shanshan Song, Shanghai (CN); Jinxue He, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 853 days.

(21) Appl. No.: 17/618,825

(22) PCT Filed: Jun. 12, 2020

(86) PCT No.: PCT/CN2020/095921
§ 371 (c)(1),
(2) Date: Dec. 13, 2021

(87) PCT Pub. No.: WO2020/249109
PCT Pub. Date: Dec. 17, 2020

(65) Prior Publication Data
US 2022/0235061 A1    Jul. 28, 2022

(30) Foreign Application Priority Data
Jun. 13, 2019  (CN) .......................... 201910511371.9

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .............................. C07D 487/04; A61P 35/00
See application file for complete search history.

(56) References Cited

U.S. PATENT DOCUMENTS

| | | |
|---|---|---|
| 2006/0183747 A1 | 8/2006 | Freyne et al. |
| 2013/0289037 A1 | 10/2013 | Langston et al. |

FOREIGN PATENT DOCUMENTS

| | | | |
|---|---|---|---|
| CN | 102924457 A | 2/2013 | |
| CN | 109535161 A | 3/2019 | |
| JP | 2008530027 A | 8/2008 | |
| JP | 2009528986 A | 8/2009 | |
| RU | 200900285 A1 | 8/2009 | |
| WO | WO-2006084281 A1 * | 8/2006 | .............. A61P 25/28 |
| WO | WO2007067559 A2 | 6/2007 | |
| WO | WO2007092213 A2 | 8/2007 | |
| WO | 2008019124 A1 | 2/2008 | |

OTHER PUBLICATIONS

Peterson, Eileen M., et al. "Synthesis and biological evaluation of 5'-sulfamoylated purinyl carbocyclic nucleosides." Journal of Medicinal Chemistry, vol. 35, No. 22, Oct. 1992, pp. 3991-4000, https://doi.org/10.1021/jm00100a003. (Year: 1992).*
JP Office Action of application No. 2021-573893 dated Feb. 7, 2023.
Asif "A brief study of various synthetic methods of triazoles derivatives and their biological potential" Mor. J. Chem. vol. 2, iss. 3, Jul. 2014, pp. 3-136, <https://revues.imist.ma/index.php/morjchem/article/view/1976> accessed May 25, 2022.
Brownell et al. "Substrate-assisted inhibition of ubiquitin-like protein-activating enzymes: the NEDD8 E1 inhibitor MLN4924 forms a NEDD8-AMP mimetic in situ" Molecular Cell, vol. 37, iss. 1, Jan. 15, 2010, pp. 102-111.
Ciapetti et al. "Molecular Variations Based on Isosteric Replacements" The Practice of Medicinal Chemistry, Jan. 2008, pp. 290-342.
International Search Report and Written Opinion for PCT CN2020095921 mailed Sep. 14, 2020, 10 pages.
Kristinsson et al. "Herbicidally Active Sulfamoyl Nucleosides Isolation and Synthesis" ACS Symposium Series, vol. 584, May 5, 1995, pp. 206-219.
Office Action mailed May 19, 2022 with respect to Chinese App No. 201910511371.9 (w/ English Translation), 11 pages.
Partial Supplementary European Search Report for EP 20823330.4 mailed May 13, 2022, 14 pages.

(Continued)

Primary Examiner — Kortney L. Klinkel
Assistant Examiner — Donna M Nestor
(74) Attorney, Agent, or Firm — Quarles & Brady LLP

(57) ABSTRACT

The present disclosure relates to triazolopyrimidine compounds and salts, compositions and uses thereof, and the triazolopyrimidine compounds have the structures represented by the formula (I):

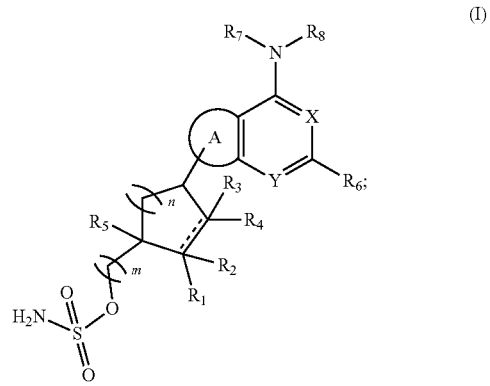

the above-mentioned triazolopyrimidine compounds have good activity and high selectivity for NAE.

10 Claims, No Drawings

(56) References Cited

OTHER PUBLICATIONS

Peterson et al. "Synthesis and Biological Evaluation of 5'-Sulfamoylated Puriny Carbocyclic Nucleosides" J.Med.Chem. vol. 35, Oct. 1, 1992, pp. 3991-4000.
Somu et al. "Antitubercular Nucleosides That Inhibit Siderophore Biosynthesis: SAR of the Glycosyl Domain" J.Med.Chem, vol. 49, iss. 26 Dec. 21, 2006, pp. 7623-7635 plus 21 page supplement.
Vince et al. "The synthesis and biological evaluation of sulfamoyl nucleosides related to carbovir and AZT" Nucleosides and Nucleotides, vol. 14, iss. 9-10, 1995, pp. 2051-2060.
Xu et al. "Reaction intermediate analogues as bisubstrate inhibitors of pantothenate synthetase" Bioorganic & Medicinal Chemistry, vol. 22, iss. 5, Mar. 1, 2014, pp. 1726-1735.
Russian Notice of Allowance dated Nov. 7, 2023; English language translation attached; Russian application No. 2022100250.
CAS Registry [Online] Chemical Abstracts Service, Columbus, Ohio, US; "907549-62-6", Database accession No. 907549-62-6, entered Sep. 19, 2006.
CAS Registry [Online] Chemical Abstracts Service, Columbus, Ohio, US; "907549-70-6", Database accession No. 907549-70-6, entered Sep. 19, 2006.
CAS Registry [Online] Chemical Abstracts Service, Columbus, Ohio, US; "908078-34-2", Database accession No. 908078-34-2, entered Sep. 21, 2006.
CAS Registry [Online] Chemical Abstracts Service, Columbus, Ohio, US; "908078-37-5", Database accession No. 908078-37-5, entered Sep. 21, 2006.
CAS Registry [Online] Chemical Abstracts Service, Columbus, Ohio, US; "908811-75-6", Database accession No. 908811-75-6, entered Sep. 27, 2006.

* cited by examiner

TRIAZOLOPYRIMIDINE COMPOUND AND SALT, COMPOSITION AND USE THEREOF

CROSS-REFERENCE TO RELATED APPLICATION

This application claims priority to and is a 35 U.S.C. § 371 national phase application of PCT/CN2020/095921 filed on Jun. 12, 2020, which claims the priority benefit of Chinese Patent Application No. 201910511371.9, titled "Triazolopyrimidine compounds and salts, compositions and uses thereof" and filed on Jun. 13, 2019. The entireties of both applications are incorporated by reference herein for all purposes.

TECHNICAL FIELD

The present disclosure relates to the technical field of medicinal chemistry, in particular to triazolopyrimidine compounds and salts, compositions and uses thereof.

BACKGROUND

In eukaryotic cells, a ubiquitin-proteasome system (UPS) mediates the degradation of intracellular proteins, maintains the dynamic equilibrium of protein in the body, and participates in the regulation of a variety of important physiological processes (cell cycle, signaling, gene transcription, apoptosis, DNA replication, and tumorigenesis, etc.). Ubiquitin molecules are covalently linked to a substrate protein through a three-step cascade catalysis by enzymes (ubiquitin activating enzyme (E1), ubiquitin conjugating enzyme (E2), and ubiquitin ligase (E3)), so that the substrate protein is identified and degraded by the proteasome. For example, UPS disorders will lead to the occurrence of many diseases. Studies have shown that UPS abnormalities are more common in tumors. Therefore, the development of anti-tumor drugs for UPS is of great significance. Bortezomib, an inhibitor of the 26S proteasome in UPS, has been marketed as a drug for multiple myeloma, which further proves that tumor can be treated by adjusting UPS. However, bortezomib is not selective in inhibiting the proteasome and shows serious adverse reactions in clinical practice.

The ubiquitin ligase E3 has a wide range of types and has a strict substrate specificity. Cullin-RING Ligase (CRL) is the largest multi-subunit ubiquitin ligase in the cell, responsible for about 20% of the protein degradation in the cell, and many of the substrate proteins of CRL, such as cdt-1, p27, pIκBα, etc., are closely related to tumor growth. Therefore, UPS can be regulated to inhibit tumor cell growth by inhibiting the activity of CRL in UPS.

As a multi-subunit ubiquitin ligase, in addition to the need of effective combination of subunits, CRL function also relies on a neddylation to its skeleton protein, the cullin protein, by a ubiquitin-like molecule, neural precursor cell-expressed develop-mentally down-regulated 8 (NEDD8). NEDD8 activating enzyme (NAE) is the only activating enzyme in the neddylation signal pathway, therefore, the CRL activity can be controlled by inhibiting the NAE activity, the specific substrate proteins are increased so that the growth of tumor cells is inhibited, thereby achieving the goal of tumor treatment. The NAE inhibitor targets the neddylation process in CRL activation, and has a higher selectivity and better safety, compared with bortezomib.

SUMMARY

Based on this, it is necessary to provide a triazolopyrimidine compound and a salt, a composition and a use thereof that have good activity and high selectivity for NAE.

A triazolopyrimidine compound has a structure represented by the formula (I):

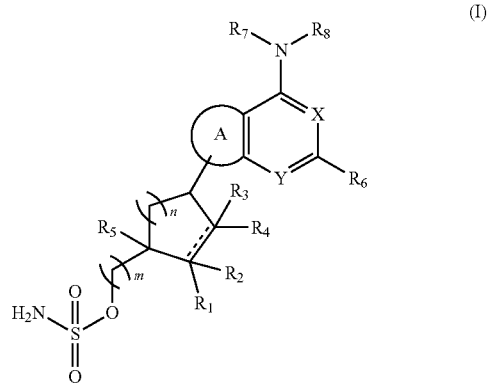

wherein, ring A is a five- or six-membered ring, and the ring A contains at least two N atoms;

X and Y are each independently C or N;

$R_1$, $R_2$, $R_3$, $R_4$, $R_5$ and $R_6$ are each independently selected from the group consisting of: H, substituted or unsubstituted alkyl, substituted or unsubstituted alkoxy, substituted or unsubstituted cycloalkyl, substituted or unsubstituted heterocyclyl, substituted or unsubstituted aryl, substituted or unsubstituted heteroaryl, silicyl, ketone group, carbonyl, carboxyl, ester group, alkoxycarbonyl, aryloxycarbonyl, amino group, cyano group, carbamoyl, haloformyl, isocyano-group, isocyana te group, tiocyanate group, isothiocyanate group, hydroxyl, nitro group and halogen;

any two or more of $R_1$, $R_2$, $R_3$, and $R_4$ may be connected to form a spiro ring, a bridged ring or a fused ring, and the spiro ring, the bridged ring or the fused ring optionally contains 0 or more heteroatoms;

⚡ represents a single bond or a double bond;

when ⚡ is the double bond, one of the substituents $R_1$ and $R_2$ does not exist, and one of the substituents $R_3$ and $R_4$ does not exist;

$R_7$ and $R_8$ are each independently selected from the group consisting of: H, substituted or unsubstituted linear alkyl, substituted or unsubstituted branched alkyl, substituted or unsubstituted cycloalkyl, substituted or unsubstituted heterocyclyl, substituted or unsubstituted aryl, and substituted or unsubstituted heteroaryl;

$R_7$ and $R_8$, together with a nitrogen atom to which the $R_7$ and $R_8$ are connected, can optionally form a three- to eight-membered heterocyclyl or a five- to ten-membered heteroaryl;

m is an integer of 1 to 20;

n is 1, 2, 3, or 4.

In one embodiment, the ring A contains three N.

In one embodiment, m is 1, 2, 3, 4, 5, 6, 7, or 8.

In one embodiment, n is 1 or 2.

In one embodiment, at least one of $R_7$ and $R_8$ is H.

In one embodiment, the triazolopyrimidine compound has a structure represented by the formula (II):

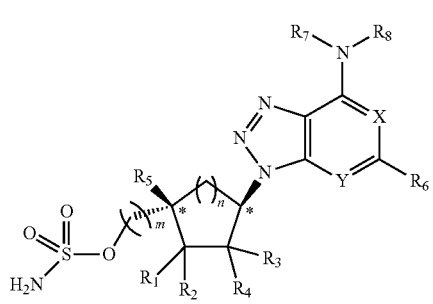

(II)

wherein, at least one of X and Y is N.

In one embodiment, X and Y are both N.

In one embodiment, the triazolopyrimidine compound has a structure represented by the formula (II 1):

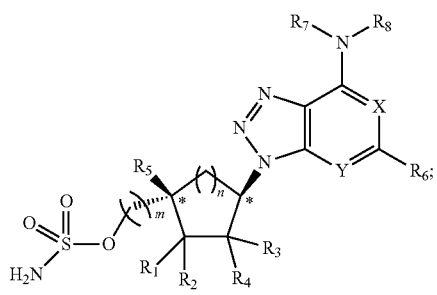

(II-1)

$R_1$, $R_2$, $R_3$, $R_4$, $R_5$, $R_6$, $R_7$ or $R_8$ are as defined above;
n, m, X and Y are as defined above.

In one embodiment, the triazolopyrimidine compound has a structure represented by the formula (III):

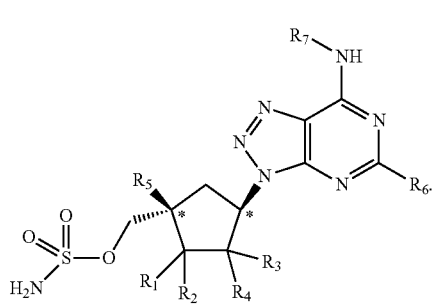

(III)

In one embodiment, the triazolopyrimidine compound has a structure represented by the formula (III-1):

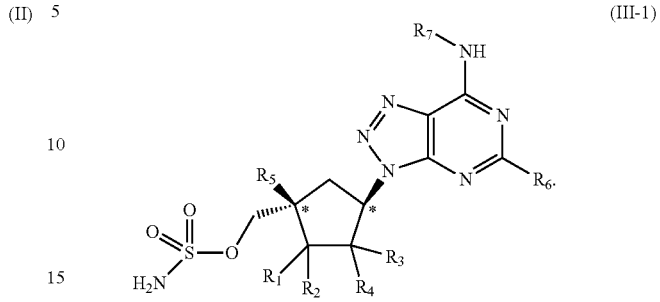

(III-1)

In one embodiment, $R_1$, $R_2$, $R_3$, $R_4$ and $R_6$ are each independently selected from the group consisting of: hydrogen atom, hydroxyl, amino group, halogen, C1-C8 alkyl, three- to eight-membered cycloalkyl, amide, and ester group, wherein C1-C8 alkyl and three- to eight-membered cycloalkyl are optionally substituted with one or more hydroxy, hydroxymethyl or halogen;

$R_5$ is selected from the group consisting of hydrogen atom, hydroxyl, amino group and halogen.

In one embodiment, the triazolopyrimidine compound has a structure represented by the formula (IV):

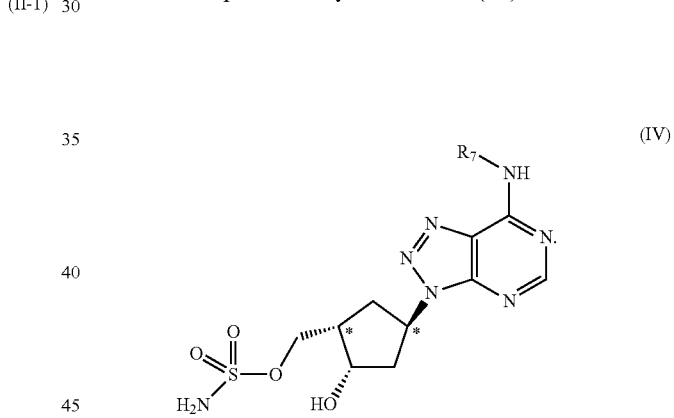

(IV)

In one embodiment, the triazolopyrimidine compound has a structure represented by the formula (IV-1):

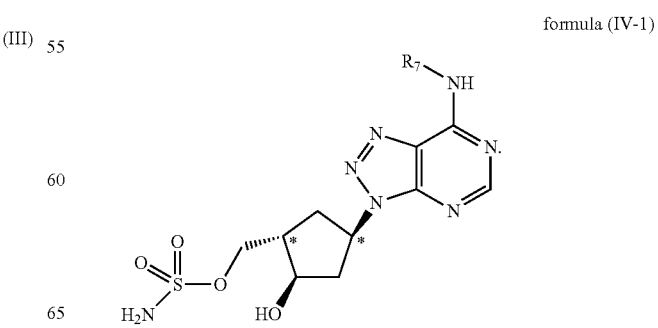

formula (IV-1)

In one embodiment, the triazolopyrimidine compound has a structure represented by the formula (IV-2):

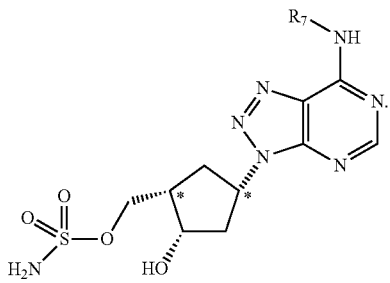

formula (IV-2)

In one embodiment, R₇ is C1-C20 linear alkane, C1-C20 branched alkane, three- to ten-membered saturated cycloalkyl, three- to ten-membered unsaturated cycloalkyl, or substituents represented by the following structural formulas (V-1) to (V-4):

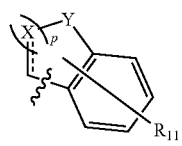

(V-1)

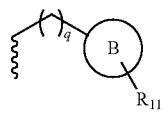

(V-2)

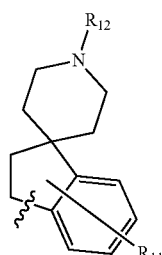

(V-3)

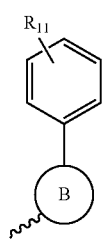

(V-4)

wherein, X and Y are each independently C or N;

⌇ represents a single bond or a double bond;

ring B is selected from the group consisting of: three- to eight-membered cycloalkane, benzene ring, thiophene ring, furan ring, pyrazole ring, imidazole ring, pyran ring, pyrrole ring, thiazole ring and oxazole ring;

p is 1 or 2;

q is 0, 1, 2, 3, 4, 5, 6, 7 or 8;

$R_{11}$ is selected from the group consisting of: substituted or unsubstituted alkyl, substituted or unsubstituted alkoxy, substituted or unsubstituted cycloalkyl, substituted or unsubstituted heterocyclyl, substituted or unsubstituted aryl, substituted or unsubstituted heteroaryl, silicyl, ketone group, carbonyl, ester group, amino group, alkoxycarbonyl, aryloxycarbonyl, cyano group, carbamoyl, haloformyl, isocyano-group, isocyanate group, tiocyanate group, isothiocyanate group, hydroxyl, nitro group and halogen;

$R_{12}$ is selected from the group consisting of hydrogen atom, C1-C6 alkyl, alkoxycarbonyl, alkylaminocarbonyl, and aminocarbonyl.

In one embodiment, the structural formula (V-1) has the following structure:

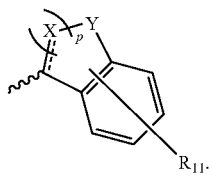

In one embodiment, X and Y in the structural formula (V-1) are both N.

In one embodiment, X and Y in the structural formula (-1) are both C.

In one embodiment, the structural formula (V-3) has the following structure:

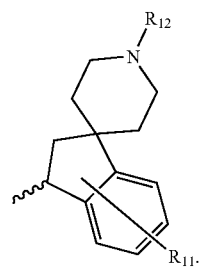

In one embodiment, the structural formula (V-4) has the following structure:

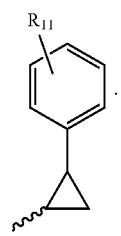

In one embodiment, $R_{11}$ is selected from the group consisting of: C1-C6 linear alkyl, C1-C6 branched alkyl, C1-C6 alkoxy, three- to eight-membered cycloalkyl, three- to eight-membered heterocyclyl, aryl, heteroaryl, silyl, ketone group, carbonyl, ester group, alkoxycarbonyl, aryloxycarbonyl, cyano group, carbamoyl, haloformyl, hydroxyl, nitro group, and halogen; wherein the C1-C6 linear alkyl, C1-C6 branched alkyl, C1-C6 alkoxy, three- to eight-membered cycloalkyl, three- to eight-membered heterocyclyl, aryl, and heteroaryl are optionally substituted with one or more alkyl, alkoxy, hydroxyl, cyano group, amino group, nitro group or halogen.

In one embodiment, $R_{11}$ is halogen, hydroxyl,

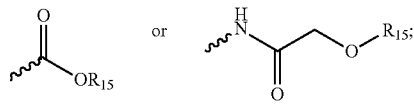

$R_{15}$ is hydrogen atom or C1-C6 alkyl.

In one embodiment, $R_7$ is selected from the following groups:

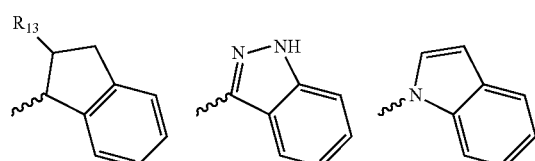

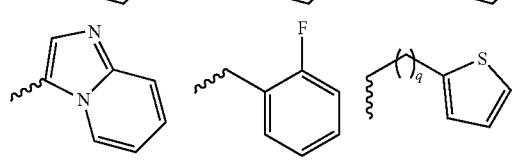

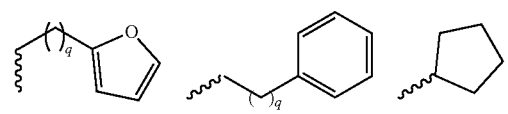

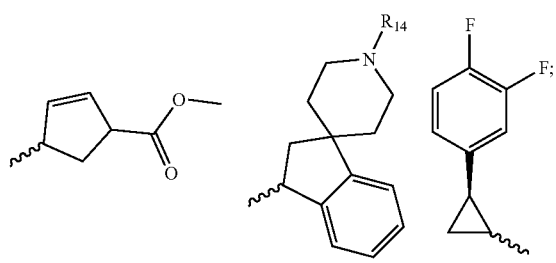

wherein, $R_{13}$ is selected from the group consisting of the following groups: hydrogen atom, hydroxyl, $C_1$-$C_6$ alkoxy group and

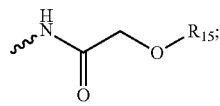

$R_{14}$ is selected from the group consisting of hydrogen atom, C1-C6 alkyl and -Boc;

$R_{15}$ is selected from the group consisting of hydrogen atom and C1-C6 alkyl;

q is 0, 1, 2, 3, or 4.

In one embodiment, the triazolopyrimidine compound is optionally selected from compounds having the following structures:

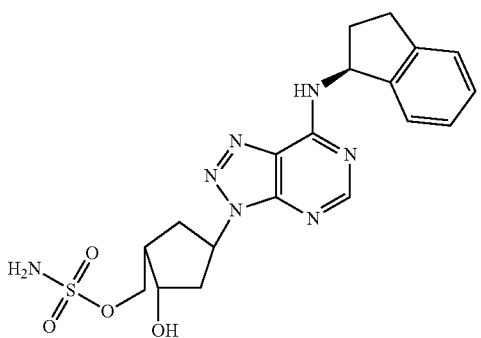

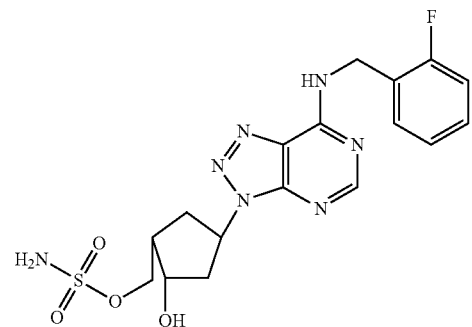

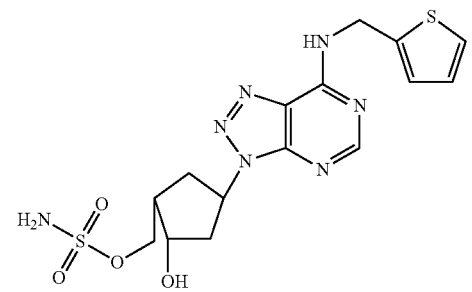

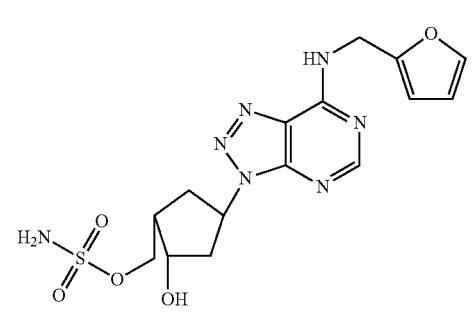

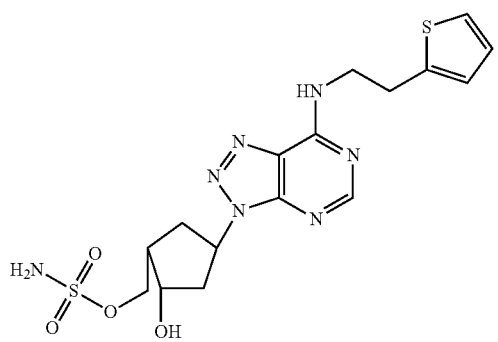

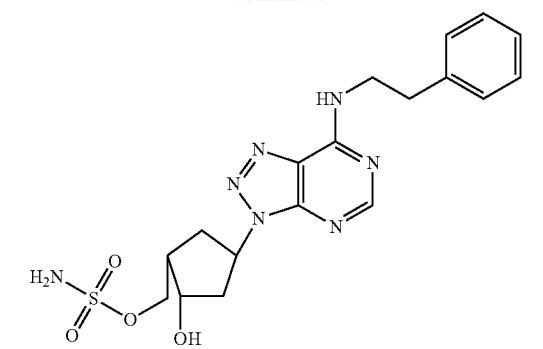
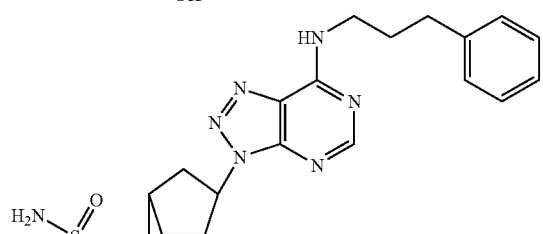
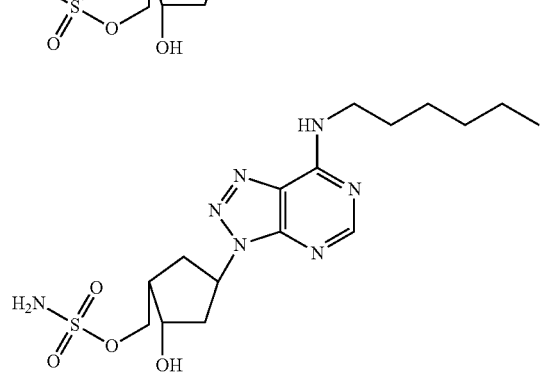
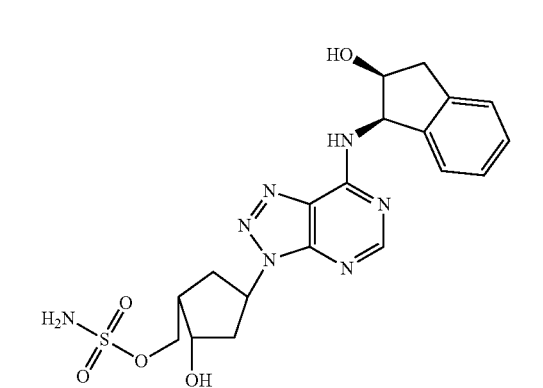
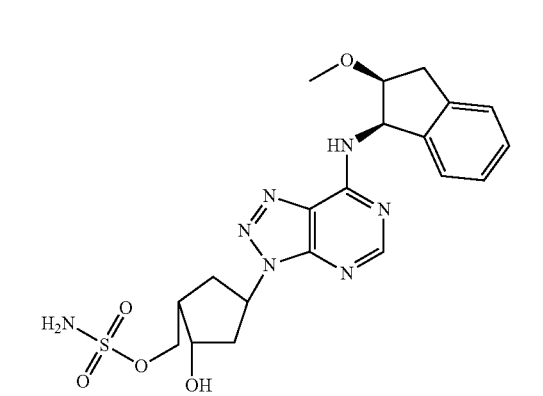
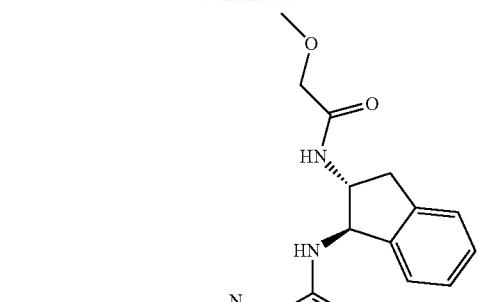
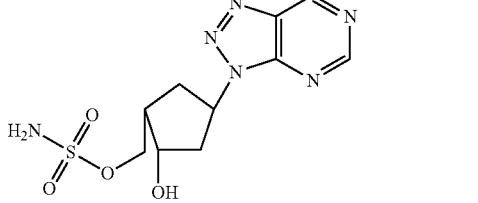
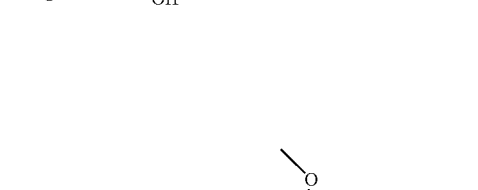
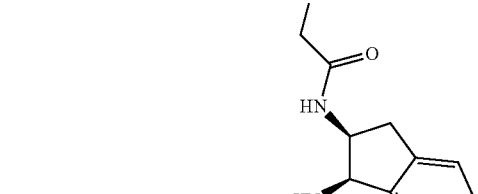
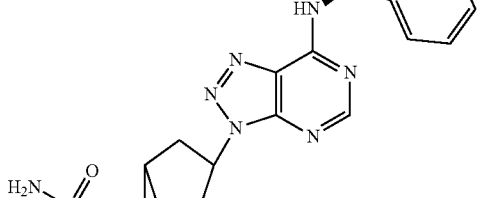
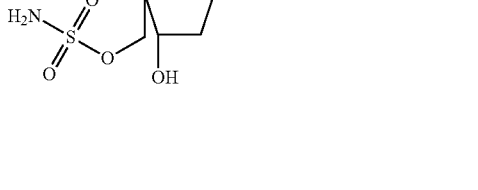
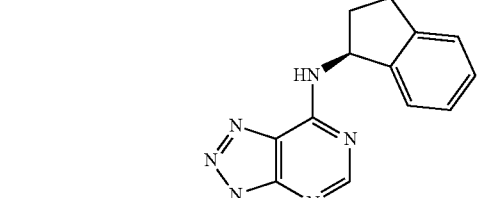
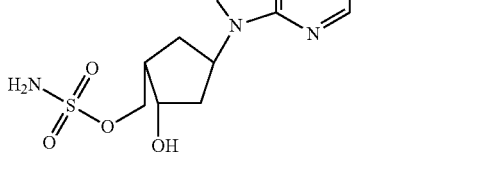

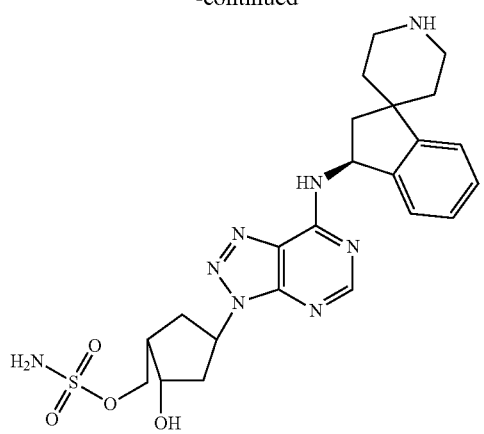
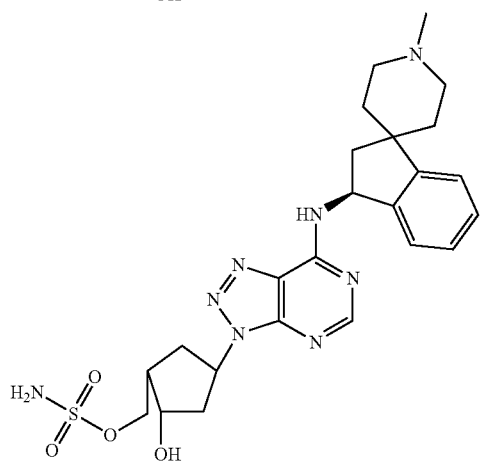
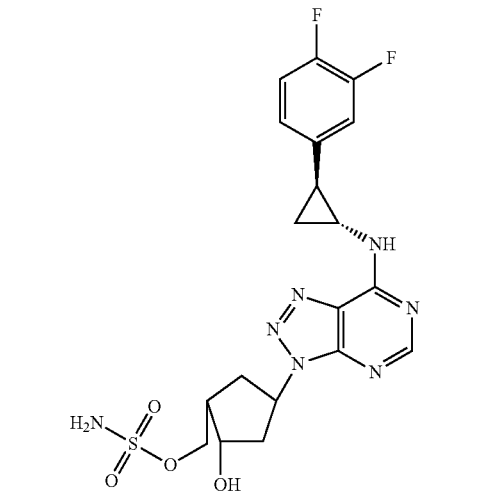
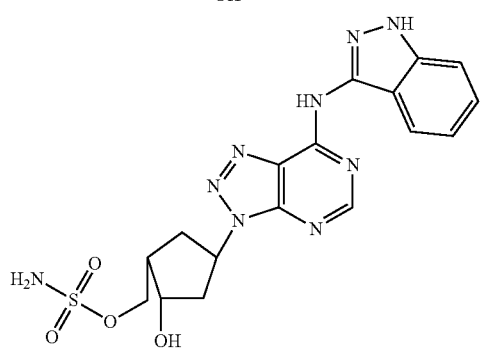

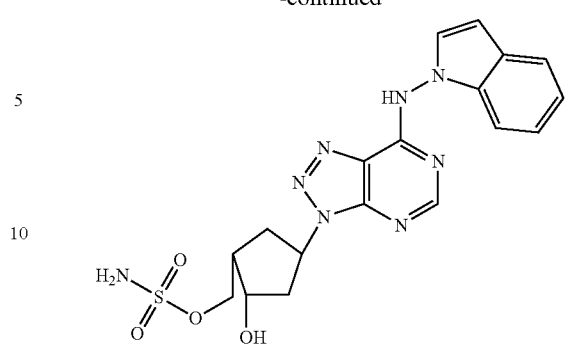
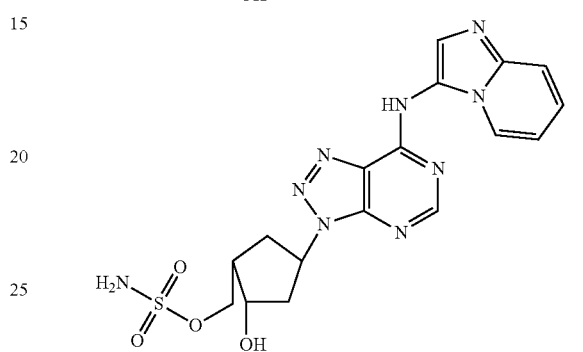
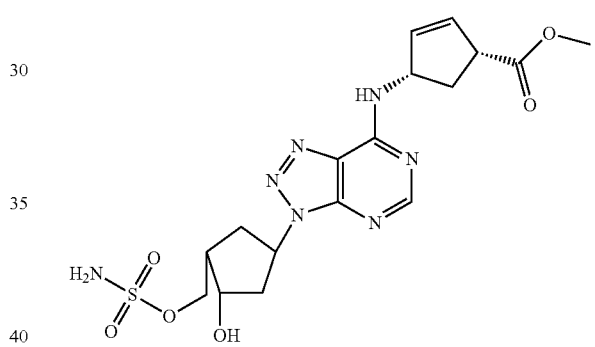
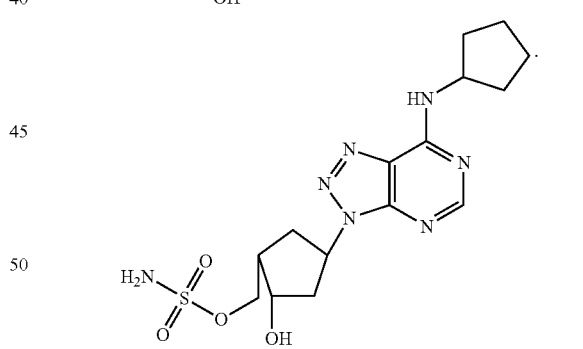

A method for preparing the above-mentioned triazolopyrimidine compound includes the following steps:

providing a compound having the structure represented by the formula (I-1);

reacting the compound having the structure represented by the formula (I-1) with $NHR_7R_8$ to obtain a compound having the structure represented by the formula (I-2); and reacting the compound having the structure represented by the formula (I-2) with sulfamyl chloride to obtain a triazolopyrimidine compound represented by the formula (I);

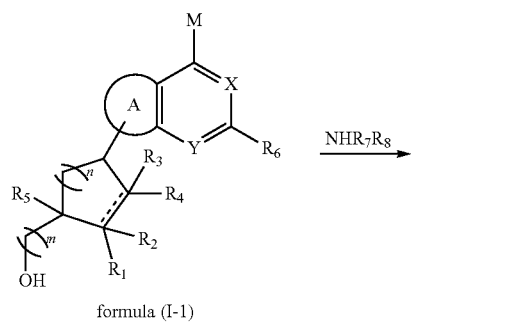

formula (I-1)

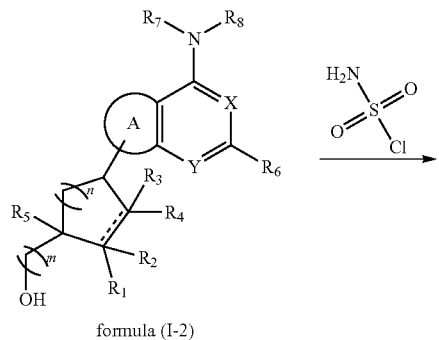

formula (I-2)

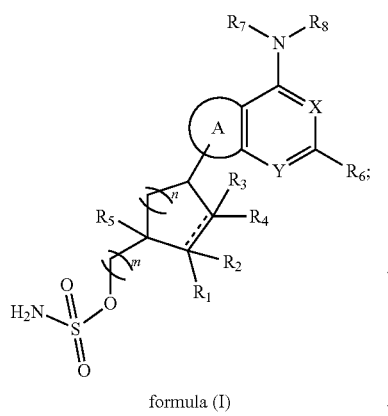

formula (I)

wherein, M represents a halogen.

In one embodiment, the step of providing a compound having the structure represented by the formula (-1) includes the following step:

reacting a compound represented by the formula (I-3) with a compound represented by the formula (I-4) to obtain a compound having the structure represented by the formula (I-1).

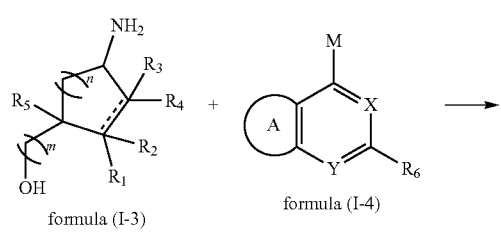

formula (I-3)     formula (I-4)

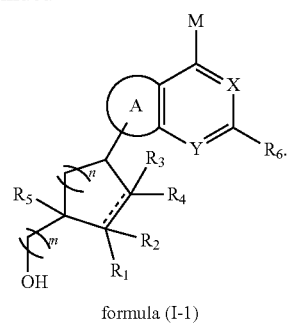

formula (I-1)

In one embodiment, the compound of formula (IV) is synthesized by the following route:

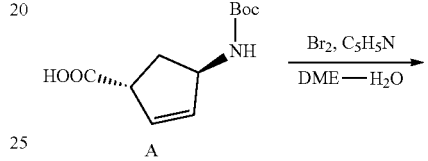

A

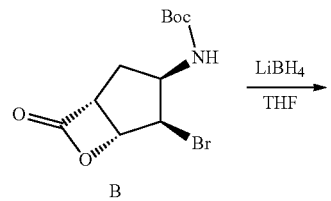

B

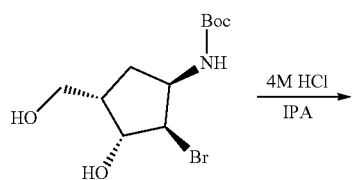

C

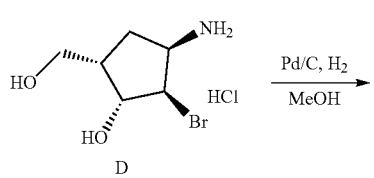

D

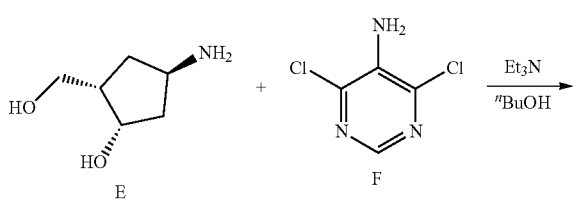

E     F

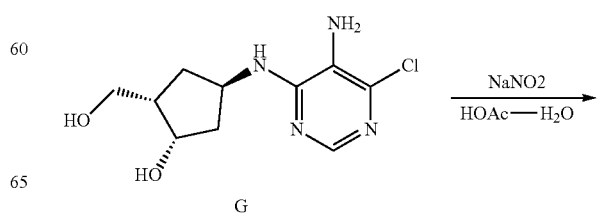

G

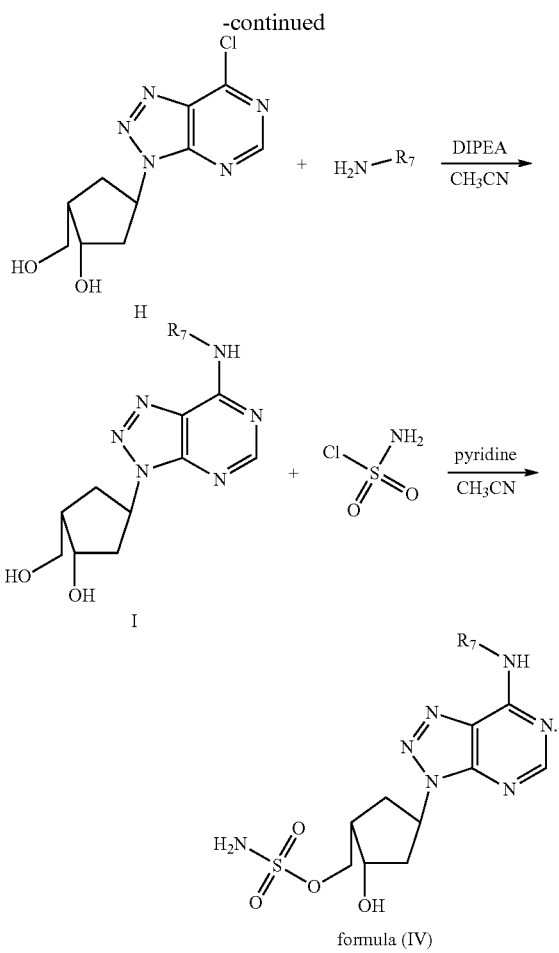

formula (IV)

A triazolopyrimidine salt prepared from the above-mentioned triazolopyrimidine compound and a pharmaceutically acceptable salt.

In one embodiment, the pharmaceutically acceptable salt is an inorganic acid salt or an organic salt, wherein, the inorganic salt is selected from: hydrochloride, hydrobromide, nitrate, sulfate or phosphate; and the organic acid salt is selected from: formate, acetate, propionate, benzoate, maleate, fumarate, succinate, tartrate, citrate, alkyl sulfonate or aryl sulfonate.

In one embodiment, the alkyl sulfonate is methyl sulfonate or ethyl sulfonate; and the aryl sulfonate is benzene sulfonate or p-toluene sulfonate.

A triazolopyrimidine solvate includes the above-mentioned triazolopyrimidine compound and a solvent.

In one embodiment, the solvent is one or more selected from water, ethanol, isopropanol, ether, or acetone.

A composition includes the above-mentioned triazolopyrimidine compound.

A triazolopyrimidine prodrug includes the above-mentioned triazolopyrimidine compound.

Use of the above-mentioned triazolopyrimidine compound, the above-mentioned triazolopyrimidine salt, the above-mentioned triazolopyrimidine solvate or the above-mentioned composition in the preparation of a medicine for treating a cell proliferation disease or an E1 activating enzyme inhibition-related disease.

In one embodiment, the cell proliferation disease is cancer or tumor, such as myelodysplastic syndrome, acute myelogenous leukemia, chronic myeloid leukemia, non-small cell lung cancer, multiple myeloma, etc.

The above-mentioned triazolopyrimidine compounds have good activity and high selectivity for NAE, and is able to prepare a medicine for the cell proliferation disease or the E1 activating enzyme inhibition-related disease.

DETAILED DESCRIPTION OF THE EMBODIMENTS

In order to facilitate the understanding of the present disclosure, the present disclosure will be described more fully hereinafter, and preferred embodiments of the present disclosure are given below. However, the present disclosure may be embodied in many different forms and is not limited to the embodiments described herein. Rather, these embodiments are provided so that the understanding of the present disclosure will be more thorough and complete.

All technical and scientific terms used herein have the same meaning as commonly understood by skilled person in the art to which this disclosure belongs, unless otherwise defined. The terms used in the specification of the present disclosure herein are for the purpose of describing specific embodiments only and are not intended to limit the present disclosure. The term "and/or" used herein includes any and all combinations of one or more of the associated listed items.

Definitions and General Terms

Unless stated to the contrary, the following terms used in the description and claims have the following meanings.

In the present disclosure, the term "optionally substituted with one or more substituents" means substituted with one or more substituents, or unsubstituted. Specifically, "optional" or "optionally" means that the event or environment described later may occur, but doesn't have to occur, and the description includes the occasion where the event or environment occurs or does not occur. For example, "C1-C8 alkyl is optionally substituted with one or more hydroxyls" means that the hydroxyl may, but doesn't have to occur. This description includes the case where C1-C8 alkyl is substituted with hydroxyl and the case where C1-C8 alkyl is not substituted with hydroxyl.

"Alkyl" refers to a saturated aliphatic hydrocarbon group, including linear chain and branched chain groups. The $C_1$-$C_6$ alkyl refers to an alkyl containing 1 to 6 carbon atoms. Non-limiting examples include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, and 2,3-dimethylbutyl. The $C_1$-$C_4$ alkyl refers to an alkyl containing 1 to 4 carbon atoms. In one embodiment, "$C_1$-$C_4$ alkyl" is methyl, ethyl, n-propyl, isopropyl, n-butyl, isobutyl, t-butyl, or sec-butyl. The alkyl may be substituted or unsubstituted, and when substituted, the substituent may substitute at any available connecting position.

"Cycloalkyl" refers to a saturated or partially unsaturated monocyclic or polycyclic cyclic hydrocarbon substituent. The three- to eight-membered cycloalkyl refers to contain 3 to 8 carbon atoms. In one embodiment, three- to eight-membered monocyclic cycloalkyl is cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. The polycyclic cycloalkyl includes spiro, fused and bridged cycloalkyls. The cycloalkyl may be optionally substituted with one or more substituents.

"Spirocycloalkyl" refers to a polycyclic group that shares one carbon atom (called a spiro atom) between single rings, which can contain one or more double bonds, but none of the rings have a fully conjugated π-electron system. According to the number of spiro atoms shared between rings, a spirocycloalkyl is classified into a monospirocycloalkyl, a bispirocycloalkyl or a polyspirocycloalkyl, preferably a monospirocycloalkyl and a bispirocycloalkyl, more preferably, a four-membered/four-membered, four-membered/five-membered, four-membered/six-membered, five-membered/five-membered, or five-membered/six-membered monospirocycloalkyl.

"Fused cycloalkyl" refers to a full-carbon polycyclic group in which each ring in the system shares an adjacent pair of carbon atoms with other rings in the system, wherein one or more of the rings may contain one or more double bonds, but none of the rings have a fully conjugated π-electron system. According to the number of constituent rings, it may be divided into bicyclic, tricyclic, tetracyclic or polycyclic fused cycloalkyl, preferably bicyclic or tricyclic fused cycloalkyl, more preferably five-membered/five-membered, five-membered/six-membered, or six-membered/six-membered bicycloalkyl.

"Bridged cycloalkyl" is a full-carbon polycyclic group in which any two rings share two carbon atoms that are not directly connected, which may contain one or more double bonds, but none of the rings have a fully conjugated π-electron system. According to the number of constituent rings, it may be classified into bicyclic, tricyclic, tetracyclic or polycyclic bridged cycloalkyl, preferably bicyclic, tricyclic or tetracyclic, and more preferably bicyclic or tricyclic bridged cycloalkyl.

The cycloalkyl ring of the aforementioned "cycloalkyl", "spirocycloalkyl", ""fused cycloalkyl" or "bridged cycloalkyl" may be fused to an aryl, heteroaryl or heterocycloalkyl ring, wherein the ring connected to the parent structure is a cycloalkyl. In one embodiment, the cycloalkyl is indanyl, tetralyl, and the like.

"Heterocyclyl" refers to a saturated or partially unsaturated monocyclic or polycyclic cyclic hydrocarbon substituent, in which one or more ring atoms are selected from heteroatoms of nitrogen, oxygen or $S(O)_m$ (where m is an integer from 0 to 2), preferably a nitrogen or oxygen heteroatom; but does not include the ring part of —O—O—, —O—S— or —S—S—, and the remaining ring atoms are carbon. A four- to ten-membered heterocyclyl means that containing 4 to 10 ring atoms, of which 1 to 3 are heteroatoms; preferably, the heterocyclyl ring contains 5 to 6 ring atoms, of which 1 to 2 are heteroatoms. In one embodiment, the monocyclic heterocyclyl is dihydrofuranyl, tetrahydrofuranyl, pyrrolidinyl, piperidyl, piperazinyl, morpholinyl, thiomorpholinyl or homopiperazinyl, and the like.

In the present disclosure, the spiro ring, bridged ring or fused ring optionally contains 0 or more heteroatoms, that is, the spiro ring, bridged ring or fused ring may or may not contain heteroatoms. When it contains heteroatom(s), a "fused heterocyclyl", or "bridged heterocyclyl", etc., is formed. "Fused heterocyclyl" refers to a polycyclic heterocyclyl in which each ring in the system shares an adjacent pair of atoms with another ring in the system, one or more rings may contain one or more double bonds, but none of the rings have a fully conjugated π-electron system, where one or more ring atoms are selected from heteroatoms of nitrogen, oxygen, or $S(O)_m$ (where m is an integer from 0 to 2), and the remaining ring atoms are carbon atoms. "Bridged heterocyclyl" is a five- to fourteen-membered polycyclic heterocyclyl in which any two rings share two atoms that are not directly connected, which may contain one or more double bonds, but none of the rings have a fully conjugated π-electron system, where one or more ring atoms are selected from heteroatoms of nitrogen, oxygen, or S(O)m (where m is an integer from 0 to 2), and the remaining ring atoms are carbon atoms.

The heterocyclyl ring may be fused to an aryl, heteroaryl or cycloalkyl ring, wherein the ring connected to the parent structure is the heterocyclyl. The heterocyclyl may be optionally substituted with one or more substituents.

"Aryl" refers to a full-carbon monocyclic or fused polycyclic (that is, adjacent rings sharing pairs of carbon atoms) group with a conjugated π-electron system, preferably six- to ten-membered, more preferably phenyl and naphthyl, and most preferably phenyl. The aryl ring may be fused to a heteroaryl, heterocyclic or cycloalkyl ring, and the aryl may be substituted or unsubstituted.

A five- to ten-membered "heteroaryl" refers to a heteroaromatic system containing 1 to 4 heteroatoms and 5 to 10 ring atoms, where the heteroatom includes oxygen, sulfur, and nitrogen. The heteroaryl is preferably five-membered or six-membered, such as furyl, thienyl, pyridyl, pyrrolyl, N-alkylpyrrolyl, pyrimidinyl, pyrazinyl, imidazolyl, tetrazolyl, and the like. The heteroaryl ring may be fused to an aryl, heterocyclic or cycloalkyl ring, and the ring connected to the parent structure is the heteroaryl ring. The heteroaryl may be optionally substituted or unsubstituted.

In the present disclosure, the substituent "amino" includes primary, secondary and tertiary amino groups. Specifically, the amino group includes —$NR_{16}R_{17}$, where $R_{16}$ and $R_{17}$ are hydrogen atoms or any optional groups, for example, H, substituted or unsubstituted linear alkyl, substituted or unsubstituted branched alkyl, substituted or unsubstituted cycloalkyl, substituted or unsubstituted heterocyclyl, substituted or unsubstituted aryl, or substituted or unsubstituted heteroaryl, etc.

Alkoxy group includes —O-(alkyl) and —O-(cycloalkyl). The definitions of alkyl and cycloalkyl are as described above. In one embodiment, $C_1$-$C_4$ alkoxy group is a methoxy, ethoxy, propoxy, butoxy, cyclopropoxy or cyclobutoxy group. The alkoxy group may be optionally substituted or unsubstituted.

"Carbonyl" refers to "—CO—"; "carboxyl" refers to —COOH; "ester group" refers to "—$COOR_{17}$", and carbamoyl refers to "—$CONR_{17}R_{18}$", where $R_{17}$ and $R_{18}$ are any optional groups, for example, H, substituted or unsubstituted linear alkyl, substituted or unsubstituted branched alkyl, substituted or unsubstituted cycloalkyl, substituted or unsubstituted heterocyclyl, substituted or unsubstituted aryl, or substituted or unsubstituted heteroaryl, etc.

"Silicyl" refers to —Si(alkyl)$_3$, and the three alkyl groups connected to silicon are the same or different from each other; "hydroxyl" refers to an —OH group; "halogen" refers to fluorine, chlorine, bromine or iodine; "cyano group" refers to —CN; and "nitro group" refers to —$NO_2$.

The compounds of the present disclosure may exist in a non-solvated form and a solvated form containing a pharmaceutically acceptable solvent (such as water, ethanol, etc.), that is, including solvated and non-solvated forms.

In the present disclosure, a stereochemical configuration described by "*" in a general formula represents the relative stereochemistry;

"" indicates a connection site with the parent nucleus, for example,

indicates that any of the five carbon atoms of cyclopentane may constitute the connection site with the parent nucleus.

In the present disclosure, a certain substitutable site can be substituted with one or more substituents, and when there are multiple substituents at the substitutable site, the multiple substituents may be the same or different from each other.

"Pharmaceutical composition" represents a mixture containing one or more of the compounds described herein or physiological/medicinally available salts or prodrugs thereof and other chemical components, as well as other components. For example, physiologically/pharmaceutically acceptable carriers and excipients. The purpose of the pharmaceutical composition is to promote the administration to an organism, facilitate the absorption of active ingredients, thereby exerting the biological activity.

The excipients contained in the composition may be one or more buffers, stabilizers, antisticking agents, surfactants, wetting agents, lubricants, emulsifiers, binders, suspending agents, disintegrating agents, fillers, adsorbents, coatings (enteric or sustained-release) preservatives, antioxidants, opaque agents, glidants, processing aids, colorants, sweeteners, fragrances, flavoring agents and other known additives.

"Medicinally available salt" means "pharmaceutically acceptable salt", which refers to an organic or inorganic salt of a pharmaceutically acceptable compound.

When a compound is acidic or includes sufficiently acidic bioisosteres, appropriate "medicinally available salt" refers to a salt prepared from pharmaceutically acceptable non-toxic alkalies including inorganic alkalies and organic alkalies. The salt is derived from inorganic alkalies containing aluminum, ammonium, calcium, copper, ferrous iron, ferric iron, lithium, magnesium, manganese salt, manganese, potassium, sodium, zinc and the like. Specific embodiments include ammonium, calcium, magnesium, potassium, and sodium salts. The salt is derived from a pharmaceutically acceptable organic non-toxic base, which includes salts of primary amines, secondary amines and tertiary amines, substituted amines including naturally occurring substituted amines, cyclic amines and basic ion exchange resins such as arginine, glycine betaine, caffeine, choline, N,N'-dibenzylethylenediamine, ethanediamine, 2-diethylaminoethanol, 2-dimethylaminoethanol, ethanolamine, ethanediamine, N-ethylmorpholine, N-ethylhexahydropyridine, glucamine, aminoglucose, histidine, hydrabamine, isopropylamine, lysine, meglumine, morpholine, piperazine, piperidine, polyamine resin, procaine, purine, theobromine, triethylamine, trimethylamine, tripropylamine, tromethamine, etc.

When a compound is alkaline or includes sufficiently alkaline bioisosteres, a salt can be prepared from pharmaceutically acceptable non-toxic acids, including inorganic and organic acids. Such acids includes acetic acid, benzenesulfonic acid, benzoic acid, camphorsulfonic acid, citric acid, ethanesulfonic acid, fumaric acid, gluconic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, sulfuric acid, succinic acid, tartaric acid, p-toluenesulfonic acid, etc. Specific embodiments include citric acid, hydrobromic acid, hydrochloric acid, phosphoric acid, sulfuric acid, maleic acid, and tartaric acid. Other exemplary salts include, but are not limited to, sulfate, citrate, acetate, oxalate, chloride, bromide, iodide, nitrate, sulfate, phosphate, acid phosphate, isonicotinic acid, lactic acid, salicylate, acid citrate, tartrate, oleate, tannate, pantothenate, bitartrate, ascorbate, succinate, fumarate, maleate, gentisate, gluconate, glucuronate, saccharate, formate, benzoate, glutamate, methanesulfonate, ethanesulfonate, benzenesulfonate, p-toluenesulfonate and pamoate (for example, 1,1'-methylene-bis-(2-hydroxy-3-naphthoate)).

In addition, pharmaceutical preparations containing the compound may be tablets, capsules, oral liquids, pills, granules, powders, ointments, patches, suppositories, toroches, eye drops, eye ointments, eye ointments, ear drops, sprays, aerosols, inhalants, injections, etc.

The term "therapeutically effective amount" refers to the amount of an effective compound or pharmaceutical agent, which is the minimum amount necessary to improve, cure or treat one or more symptoms of a disease or disorder.

In addition, the compound and the pharmaceutical composition of the present disclosure can be administered alone or in combination with other agents. For a combination therapy with more than one active agents, when the active agents are in separate dosage preparations, the active agents may be administered separately or in combination. In addition, the administration of one medicament may be carried out before, simultaneously with or after the administration of another medicament. When administered in combination with other medicaments, the "effective amount" of the second medicament will depend on the type of medicine used.

The compound or the pharmaceutical composition of the present disclosure may also be included in a kit.

It should be noted that the reagents from which the specific source is not indicated in the present disclosure are conventional reagents purchased in the market.

The present disclosure will be further described below in combination with specific embodiments. These embodiments are only for the purpose of explanation, and do not limit the scope and essence of the present disclosure.

$^1$H-NMR and $^{13}$C-NMR were measured by Varian MercuryAMX type-300, type-400 or type-500 instrument; liquid bromine [$Br_2$], lithium borohydride, 10% palladium on carbon (50% wet), triethylamine, sodium nitrite, pyridine were purchased from J&K Chemica Bailingwei Chemical Reagent Company, China Pharmaceutical Reagent Co., Ltd. and Shaoyuan Technology Co., Ltd. All solvents were re-distilled before use, and the anhydrous solvents used were all obtained through drying according to standard methods; unless otherwise specified, all reactions were carried out under nitrogen protection and followed by TLC, and the post-treatments were carried out by the processes of washing with saturated sodium chloride aqueous solution and drying with anhydrous sodium sulfate; unless otherwise specified, a silica gel (200-300 mesh) column chromatography was used for the purification of products; wherein the silica gel (200-300 mesh) was produced by Qingdao Ocean Chemical Factory, and the silica gel plate GF-254 was produced by Yantai Jiangyou Silicone Development Co., Ltd.

Preparation of Intermediate H

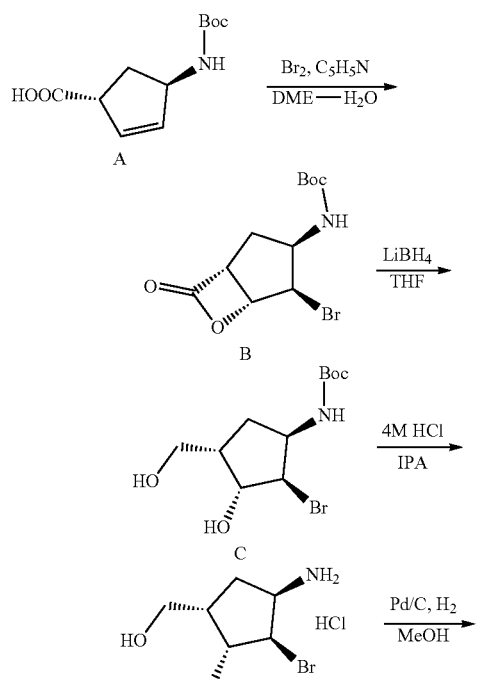

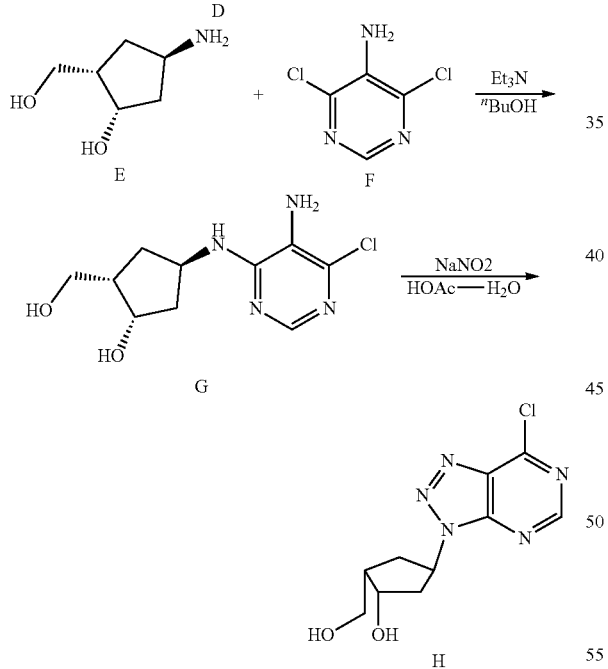

The Compound A was dissolved in DME and H$_2$O, then pyridine (2.5 eq) was added, and Br$_2$ (1.25 eq) was added to the solution at −10° C., and stirred at −10° C. for 3 hours. The reaction mixture was filtered with suction and washed with water for 3 times. The filter cake was immersed in water for 2 hours, then filtered with suction again, and then the filter cake was dried to obtain Compound B.

The Compound B was dissolved in THF, and 2M lithium borohydride in tetrahydrofuran (1 eq) was added at 0° C., and the reaction was continued. The raw materials had reacted completely after 1 hour, then the reaction was quenched by adding saturated ammonium chloride, ethyl acetate was added, and water was added for extraction, the organic layer was washed with saturated brine, dried over anhydrous sodium sulfate, dried by rotary evaporation, and Compound C was obtained by silica gel column chromatography.

The Compound C was dissolved in isopropanol, 4M HCl in methanol (6 eq) was added, and stirred at room temperature for 4 hours, then dried by rotary evaporation to obtain Compound D, which can be directly used in the next step.

The Compound D was dissolved in methanol, 10% palladium on carbon (0.2 eq) was added, and stirred for 6 hours at room temperature under a hydrogen atmosphere, then sodium carbonate was added to adjust the pH to be alkaline, the mixture was dried by rotary evaporation, and Compound E was obtained by silica gel column chromatography.

The Compound E was dissolved in n-butanol, and Compound F (1.5 eq) and triethylamine (2 eq) were added, then the mixture was reacted under microwave at 120° C. for 1 hour, dried by rotary evaporation, then Compound G was obtained by silica gel column chromatography.

The compound G was dissolved in a mixed solvent of acetic acid and water. Under an ice bath, an aqueous solution of sodium nitrite (1.2 eq) was added. After reacting for 1 hour, ethyl acetate was added for extraction. The organic layer was washed with saturated brine, dried over anhydrous sodium sulfate, and dried by rotary evaporation, then Compound H was obtained by silica gel column chromatography.

Preparation of Compound S1

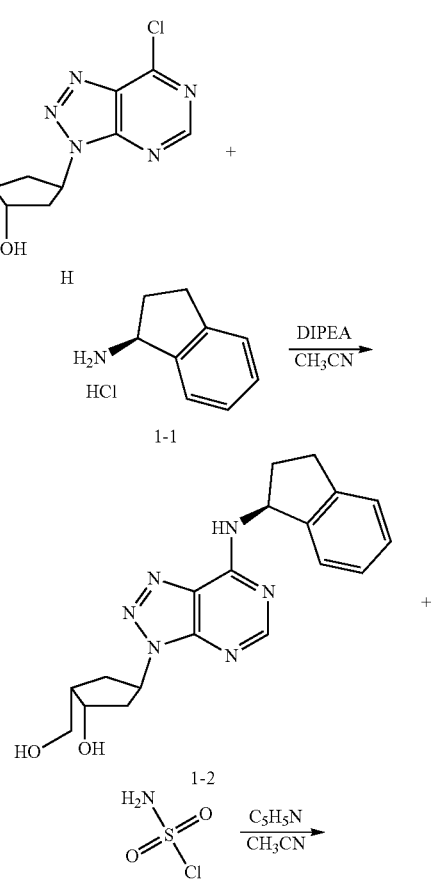

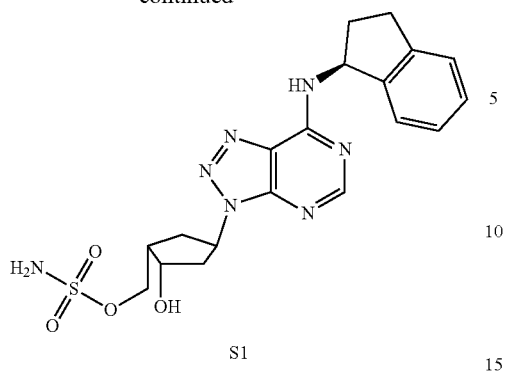

S1

Under the protection of nitrogen, the Compound H was dissolved in acetonitrile, and Compound 1-1 (1.3 eq) and DIPEA (3 eq) were added to the solution. The mixture was stirred at room temperature for 8 hours, and the raw materials were completely reacted. Then the solvent was dried by rotary evaporation, and Compound 1-2 was obtained by silica gel column chromatography (DCM:MeOH=30:1).

The Compound 1-2 was dissolved in acetonitrile, then pyridine (3 eq) and sulfamyl chloride (1.2 eq) were added to the solution at 0° C. After stirring for 2 hours, the raw materials were completely reacted. Then the solvent was dried by rotary evaporation, and Compound S1 was obtained by silica gel column chromatography (DCM:MeOH=20:1). $^1$H NMR (500 MHz, Methanol-$d_4$) δ 8.40 (s, 1H), 7.28 (d, J=7.5 Hz, 2H), 7.24 (q, J=7.8, 6.2 Hz, 1H), 7.16 (q, J=7.5, 6.2 Hz, 1H), 5.99 (t, J=7.6 Hz, 1H), 5.60 (qd, J=8.2, 4.8 Hz, 1H), 4.58 (td, J=4.6, 1.8 Hz, 1H), 4.41 (dd, J=9.8, 7.5 Hz, 1H), 4.24 (dd, J=9.8, 7.2 Hz, 1H), 3.11 (ddd, J=15.9, 8.7, 3.6 Hz, 1H), 3.00-2.87 (m, 2H), 2.71-2.55 (m, 2H), 2.45 (ddd, J=14.0, 8.0, 2.0 Hz, 1H), 2.38-2.27 (m, 2H), 2.10 (dq, J=12.9, 8.4 Hz, 1H). MS(ESI): [M+H]$^+$ m/z 446.1

Preparation of Compound S2

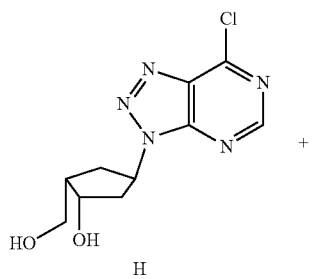

H

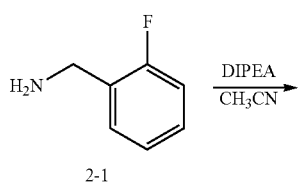

2-1

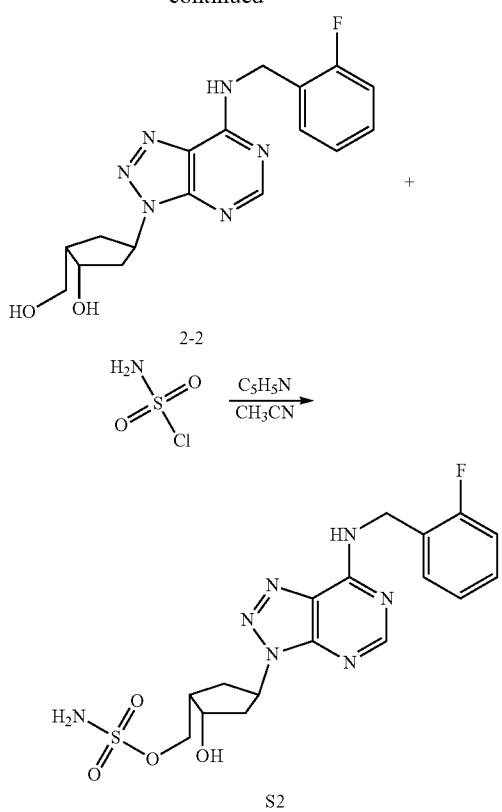

Reference was made to the Example of synthesis of Compound S1, Compound S2 was obtained by using Compound 2-1 as the raw material. $^1$H NMR (400 MHz, Methanol-$d_4$) δ 8.36 (s, 1H), 7.42 (t, J=7.5 Hz, 1H), 7.29 (q, J=7.1 Hz, 1H), 7.14-7.05 (m, 2H), 5.59 (dt, J=13.2, 6.6 Hz, 1H), 4.90 (s, 2H), 4.56 (t, J=4.6 Hz, 1H), 4.39 (dd, J=9.6, 7.6 Hz, 1H), 4.22 (dd, J=9.8, 7.2 Hz, 1H), 2.90 (s, 1H), 2.60 (ddd, J=12.9, 7.6, 4.7 Hz, 1H), 2.43 (dd, J=14.0, 8.2 Hz, 1H), 2.35-2.25 (m, 2H). MS(ESI): [M+Na]$^+$ m/z 460.2

Preparation of Compound S3

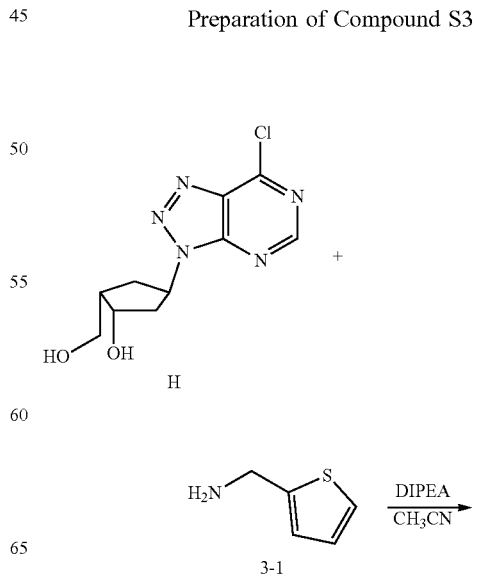

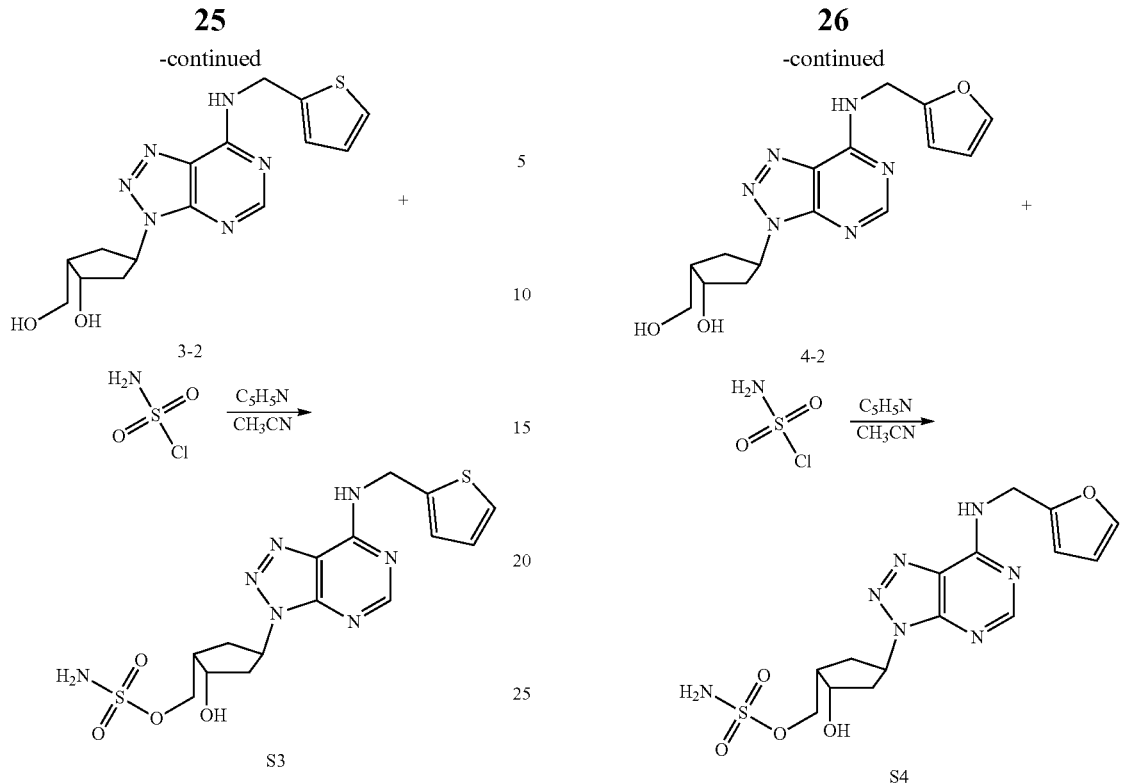

Reference was made to the Example of synthesis of Compound S1, Compound S3 was obtained by using Compound 3-1 as the raw material. $^1$H NMR (400 MHz, Methanol-$d_4$) δ 8.40 (s, 1H), 7.27 (d, J=5.1 Hz, 1H), 7.09 (d, J=3.4 Hz, 1H), 6.94 (dd, J=5.1, 3.6 Hz, 1H), 5.60 (td, J=8.0, 5.3 Hz, 1H), 5.01 (s, 2H), 4.57 (d, J=4.6 Hz, 1H), 4.39 (dd, J=9.7, 7.5 Hz, 1H), 4.22 (dd, J=9.7, 7.3 Hz, 1H), 2.90 (h, J=8.6 Hz, 1H), 2.59 (ddd, J=12.8, 7.6, 4.7 Hz, 1H), 2.43 (ddd, J=14.1, 8.2, 1.8 Hz, 1H), 2.35-2.25 (m, 2H). MS(ESI): [M+Na]$^+$ m/z 448.1

Reference was made to the Example of synthesis of Compound S1, Compound S4 was obtained by using Compound 4-1 as the raw material. $^1$H NMR (400 MHz, Methanol-$d_4$) δ 8.38 (s, 1H), 7.43 (s, 1H), 6.34 (dt, J=5.9, 3.0 Hz, 2H), 5.60 (td, J=8.1, 5.3 Hz, 1H), 4.83 (s, 2H), 4.57 (d, J=4.4 Hz, 1H), 4.39 (dd, J=9.7, 7.5 Hz, 1H), 4.22 (dd, J=9.7, 7.3 Hz, 1H), 2.96-2.83 (m, 1H), 2.59 (ddd, J=12.7, 7.5, 4.8 Hz, 1H), 2.43 (ddd, J=14.1, 8.2, 1.8 Hz, 1H), 2.38-2.24 (m, 2H). MS(ESI): [M+Na]$^+$ m/z 432.1

Preparation of Compound S4

Preparation of Compound S5

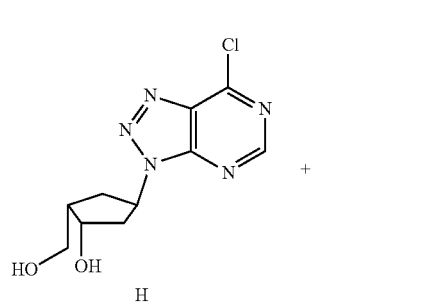

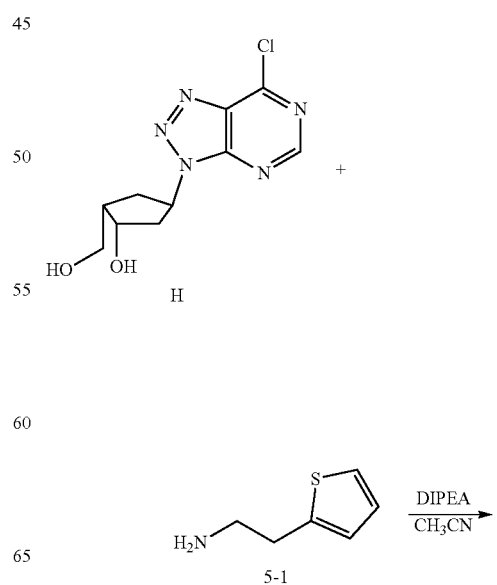

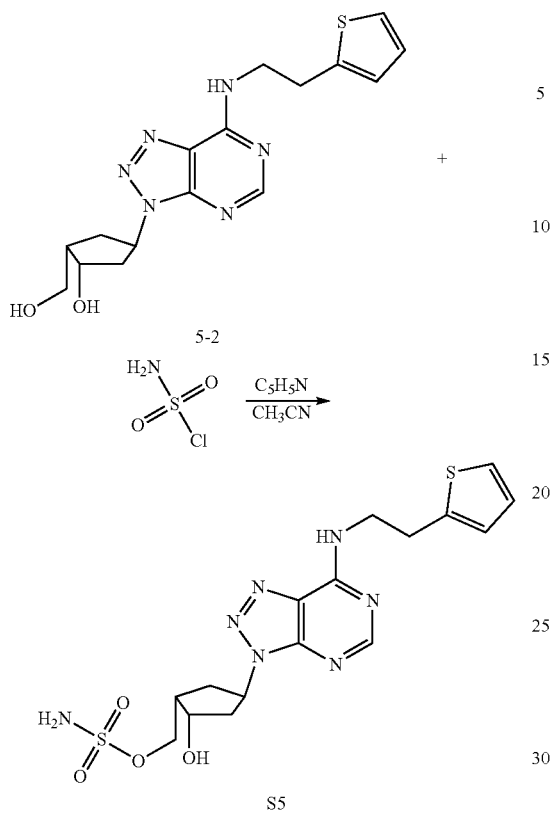

5-2

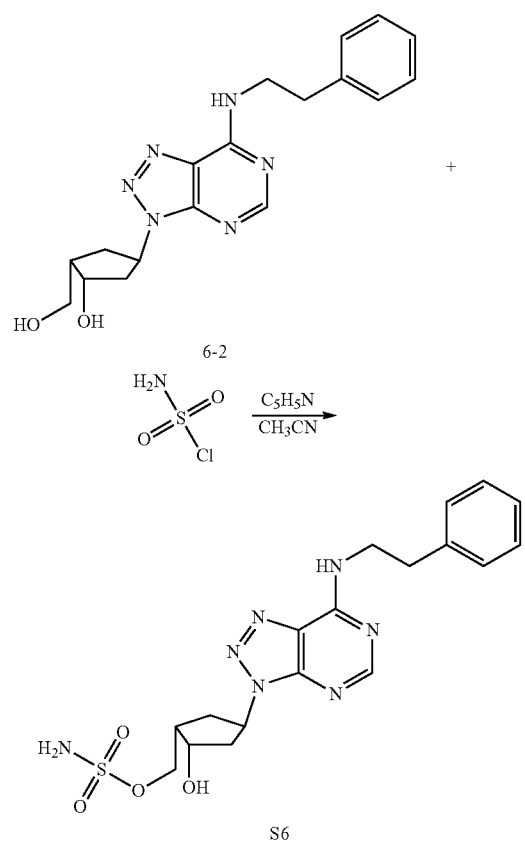

6-2

S5

S6

Reference was made to the Example of synthesis of Compound S1, Compound S5 was obtained by using Compound 5-1 as the raw material. $^1$H NMR (400 MHz, Methanol-$d_4$) δ 8.35 (s, 1H), 7.19 (dd, J=4.8, 1.6 Hz, 1H), 6.90 (s, 2H), 5.58 (qd, J=7.9, 5.0 Hz, 1H), 4.56 (t, J=4.4 Hz, 1H), 4.39 (dd, J=9.7, 7.5 Hz, 1H), 4.22 (dd, J=9.8, 7.3 Hz, 1H), 3.89 (t, J=7.2 Hz, 2H), 3.24 (q, J=7.9, 7.3 Hz, 2H), 2.90 (h, J=8.6 Hz, 1H), 2.59 (ddd, J=12.8, 7.5, 4.6 Hz, 1H), 2.48-2.38 (m, 1H), 2.37-2.23 (m, 2H). MS(ESI): [M+Na]$^+$ m/z 432.1

Reference was made to the Example of synthesis of Compound S1, Compound S6 was obtained by using Compound 6-1 as the raw material. $^1$H NMR (400 MHz, Methanol-$d_4$) δ 7.33-7.21 (m, 4H), 7.16 (dq, J=11.3, 7.1, 5.7 Hz, 1H), 5.57 (qd, J=8.0, 4.8 Hz, 1H), 4.56 (t, J=4.7 Hz, 1H), 4.45-4.35 (m, 1H), 4.31-4.17 (m, 2H), 3.85 (t, J=7.4 Hz, 2H), 3.01 (q, J=7.5 Hz, 2H), 2.89 (tt, J=11.6, 6.2 Hz, 1H), 2.59 (ddd, J=12.6, 7.6, 4.7 Hz, 1H), 2.43 (ddd, J=14.1, 8.1, 1.8 Hz, 1H), 2.37-2.24 (m, 2H). MS(ESI): [M+Na]$^+$ m/z 456.3

Preparation of Compound S6

Preparation of Compound S7

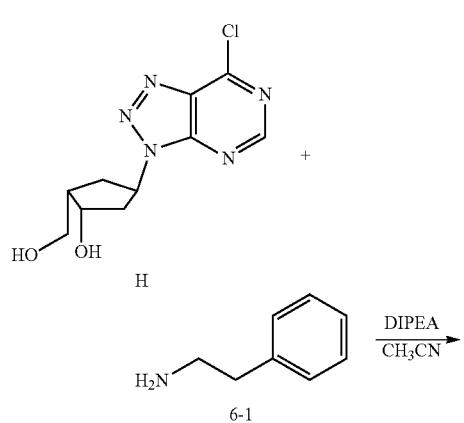

6-1

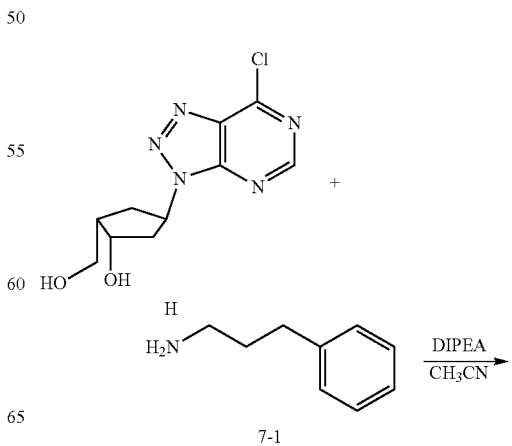

7-1

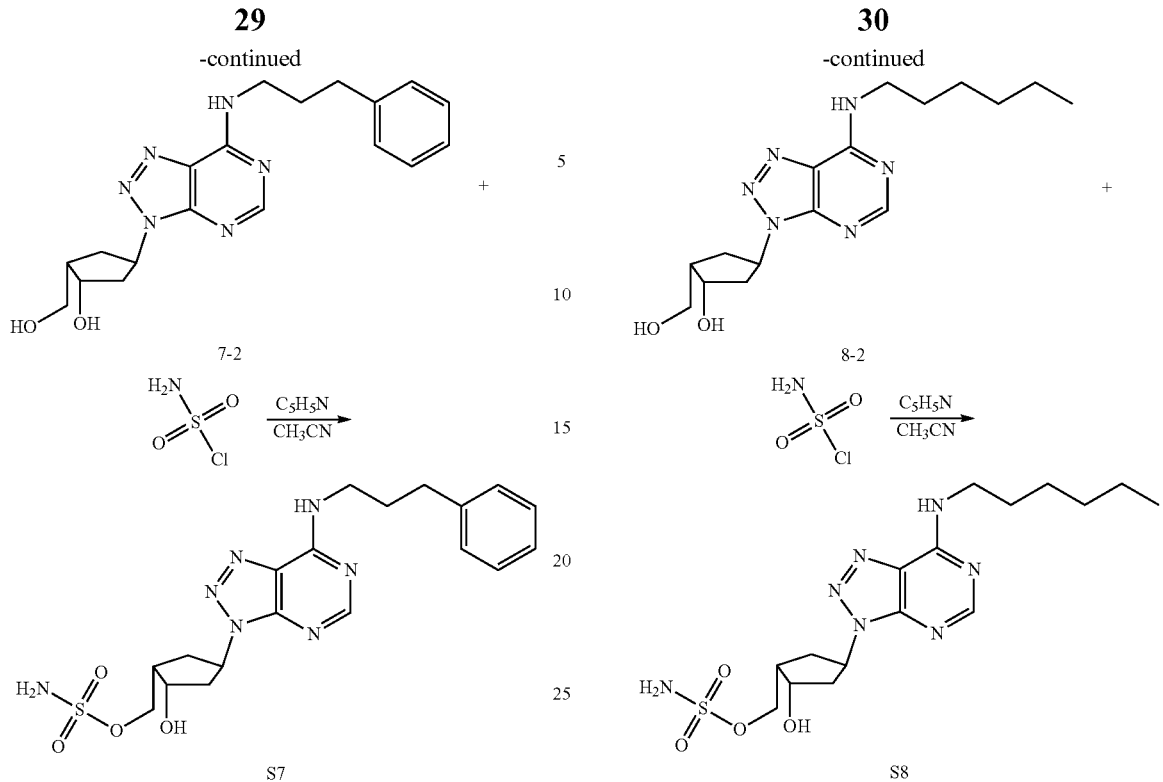

S7

S8

Reference was made to the Example of synthesis of Compound S1, Compound S7 was obtained by using Compound 7-1 as the raw material.

$^1$H NMR (400 MHz, Methanol-d$_4$) δ 8.32 (s, 1H), 7.21 (h, J=7.3 Hz, 4H), 7.12 (t, J=7.1 Hz, 1H), 5.63-5.52 (m, 1H), 4.57 (d, J=4.4 Hz, 1H), 4.39 (dd, J=9.8, 7.6 Hz, 1H), 4.22 (dd, J=9.7, 7.4 Hz, 1H), 3.65 (t, J=7.1 Hz, 2H), 2.90 (h, J=8.2 Hz, 1H), 2.74 (q, J=7.9 Hz, 2H), 2.59 (ddd, J=12.8, 7.6, 4.9 Hz, 1H), 2.46-2.37 (m, 1H), 2.30 (dd, J=11.6, 7.8 Hz, 2H), 2.03 (p, J=7.5 Hz, 2H). MS(ESI): [M+Na]$^+$ m/z 470.2

Reference was made to the Example of synthesis of Compound S1, Compound S8 was obtained by using Compound 8-1 as the raw material. $^1$H NMR (400 MHz, Methanol-d$_4$) δ 8.32 (s, 1H), 5.58 (qd, J=8.0, 5.0 Hz, 1H), 4.57 (s, 1H), 4.39 (dd, J=9.7, 7.5 Hz, 1H), 4.22 (dd, J=9.7, 7.3 Hz, 1H), 3.61 (t, J=7.2 Hz, 2H), 2.90 (ddt, J=9.7, 6.6, 3.3 Hz, 1H), 2.59 (ddd, J=14.2, 7.5, 4.7 Hz, 1H), 2.43 (ddd, J=14.0, 8.1, 1.8 Hz, 1H), 2.36-2.26 (m, 2H), 1.72 (dp, J=15.0, 7.2 Hz, 2H), 1.42 (q, J=7.7, 6.7 Hz, 2H), 1.35 (dt, J=7.5, 3.9 Hz, 4H), 0.91 (m, 3H). MS(ESI): [M+Na]$^+$ m/z 436.3

Preparation of Compound S8

Preparation of Compound S9

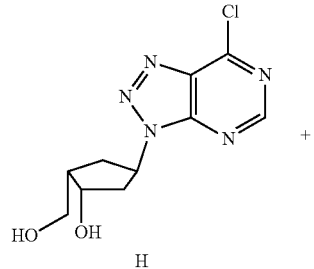

8-1

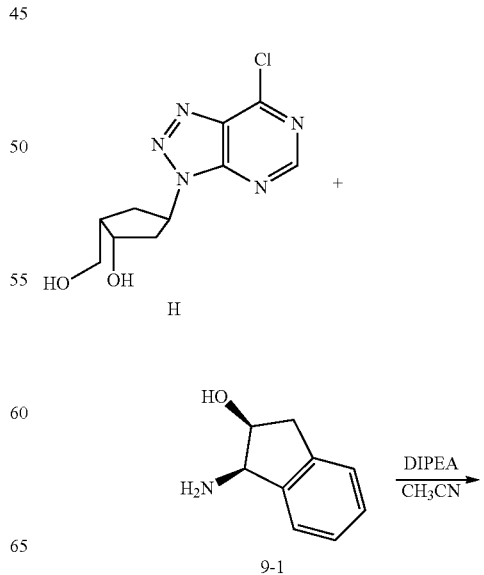

9-1

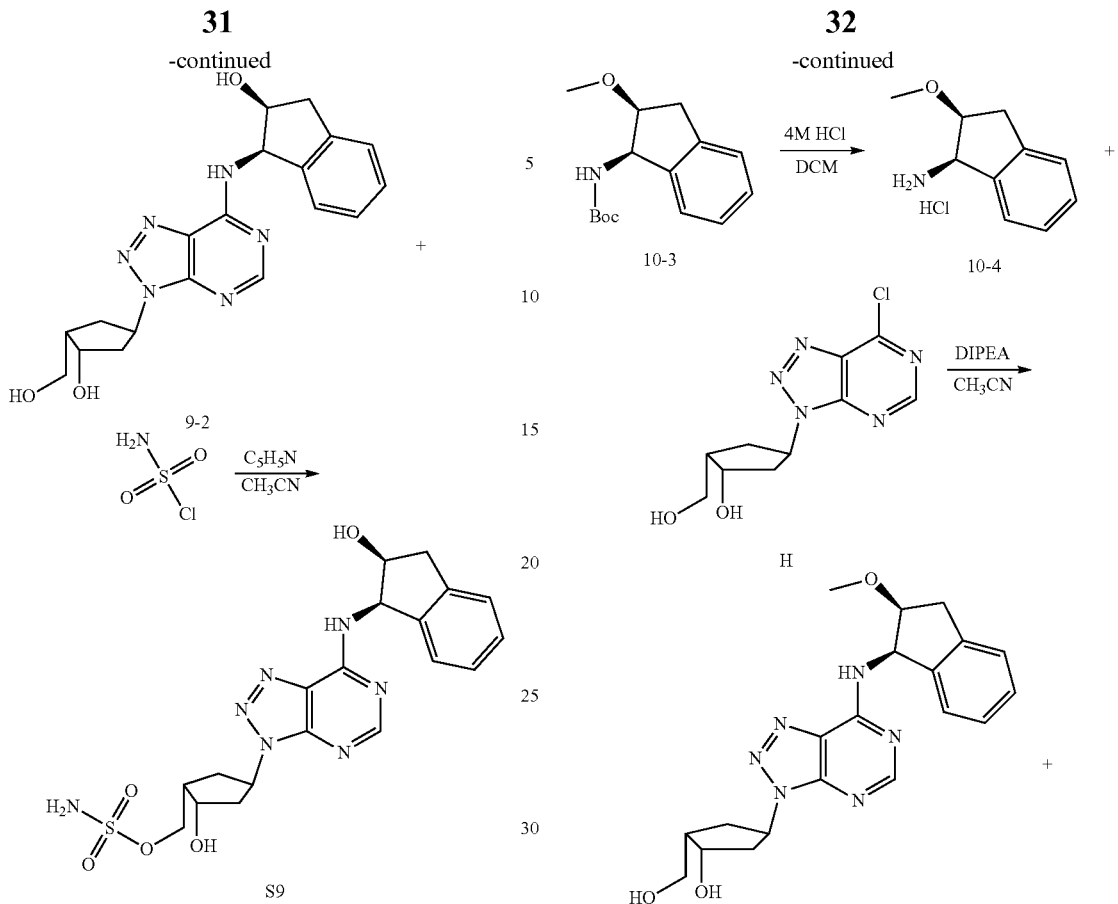

Reference was made to the Example of synthesis of Compound S1, Compound S9 was obtained by using Compound 9-1 as the raw material. $^1$H NMR (400 MHz, Methanol-$d_4$) δ 8.43 (s, 1H), 7.33-7.17 (m, 4H), 5.90 (d, J=5.0 Hz, 1H), 5.63 (qd, J=7.9, 5.1 Hz, 1H), 4.75 (td, J=5.1, 2.0 Hz, 1H), 4.58 (td, J=4.6, 1.8 Hz, 1H), 4.40 (dd, J=9.8, 7.4 Hz, 1H), 4.23 (dd, J=9.8, 7.3 Hz, 1H), 3.25 (dd, J=16.5, 5.2 Hz, 1H), 3.03 (dd, J=16.5, 2.0 Hz, 1H), 2.92 (ttd, J=9.7, 7.3, 4.3 Hz, 1H), 2.62 (ddd, J=14.1, 7.4, 4.6 Hz, 1H), 2.46 (ddd, J=14.0, 8.1, 2.0 Hz, 1H), 2.37-2.28 (m, 2H). MS(ESI): [M+H]$^+$ m/z 462.5

Preparation of Compound S10

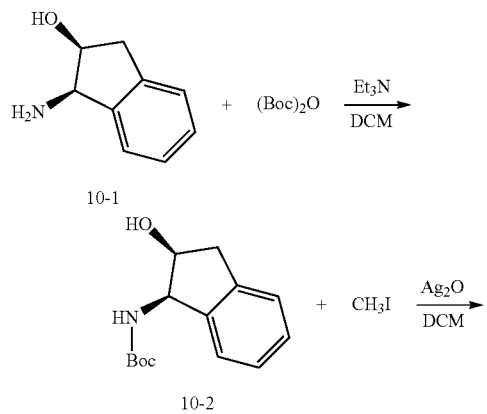

The Compound 10-1 was dissolved in acetonitrile, then triethylamine (2 eq) and BOC anhydride (1.05 eq) were added to the solution. After stirring at room temperature for 3 hours, the raw materials were completely reacted. Then the solvent was dried by rotary evaporation, and Compound 10-2 was obtained by silica gel column chromatography (DCM:MeOH=30:1).

The Compound 10-2 was added into a pressure tube filled with dichloromethane. Under the protection of nitrogen, silver oxide (5 eq) and methyl iodide (6 eq) were added to the solution. After heating and reacting at 80° C. for 30 minutes, the raw materials were completely reacted, the mixture was suction filtered with diatomaceous earth, the filtrate was dried by rotary evaporation, then Compound 10-3 was obtained by silica gel column chromatography (PE:EA=20:1).

The Compound 10-3 was dissolved in dichloromethane, and 4M HCl in dioxane was added to the reaction solution. After 30 minutes, the solvent was dried by rotary evaporation to obtain Compound 10-4.

Reference was made to the Example of synthesis of Compound S1, Compound S10 was obtained by using Compound 10-4 as the raw material. $^1$H NMR (400 MHz, Methanol-$d_4$) δ 8.45 (s, 1H), 7.35-7.14 (m, 4H), 6.00 (d, J=5.4 Hz, 1H), 5.62 (s, 1H), 4.57 (s, 1H), 4.44-4.33 (m, 2H), 4.23 (dd, J=9.8, 7.3 Hz, 1H), 3.38 (d, J=7.9 Hz, 3H), 3.17 (qd, J=16.4, 4.3 Hz, 2H), 2.91 (s, 1H), 2.61 (dt, J=12.7, 5.7 Hz, 1H), 2.46 (ddd, J=12.7, 7.8, 4.5 Hz, 1H), 2.33 (t, J=7.2 Hz, 2H). MS(ESI): [M+H]$^+$ m/z 476.4

Preparation of Compound S11

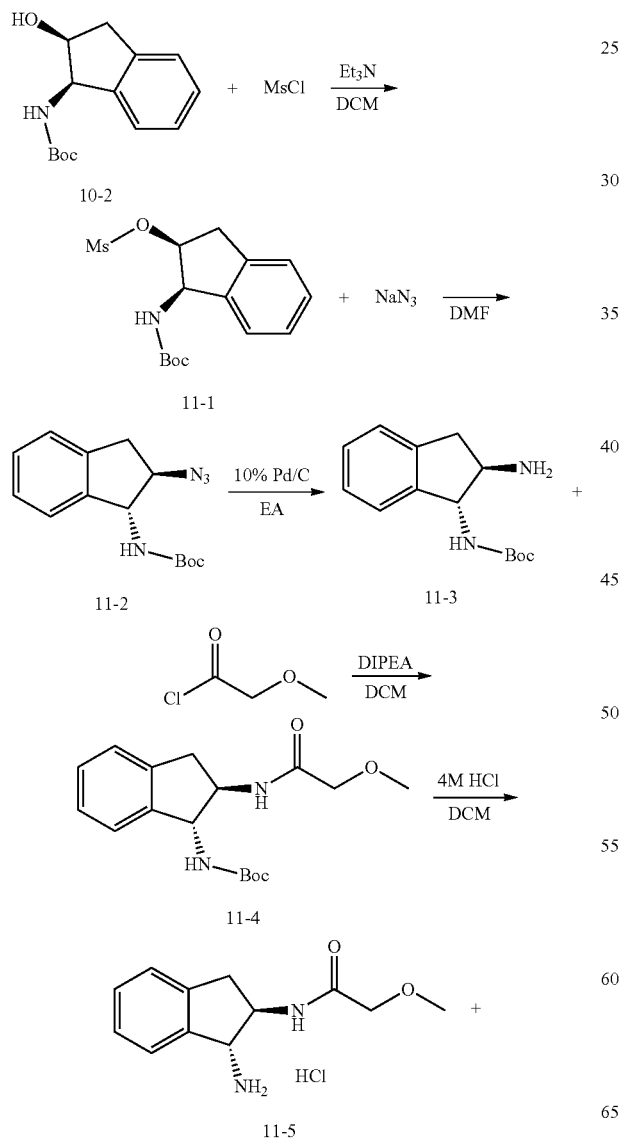

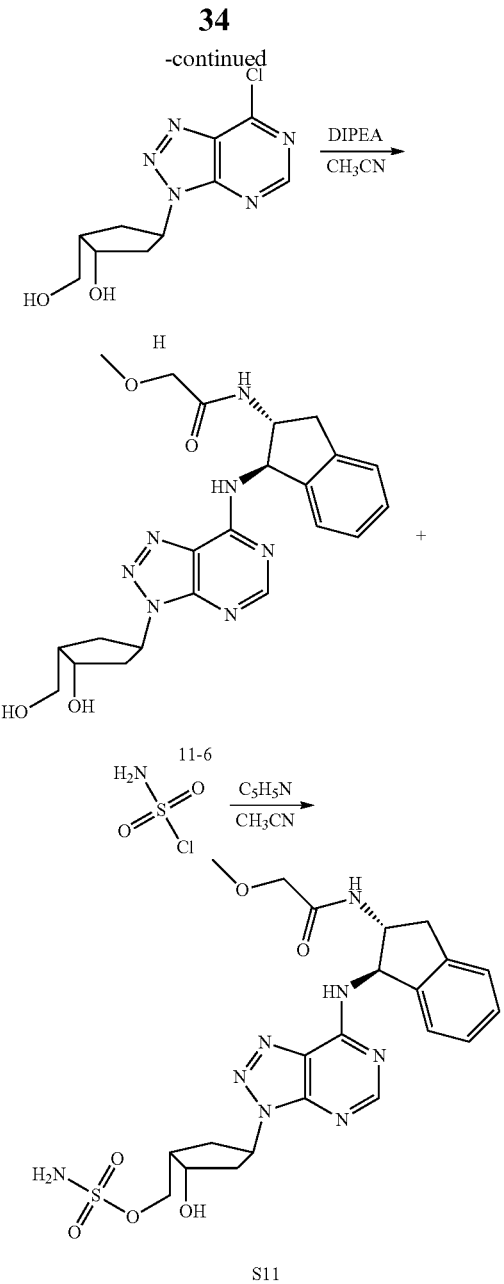

The Compound 10-2 was dissolved in dichloromethane, and triethylamine (1.5 eq) was added to the solution. Then methylsufonyl chloride (1.1 eq) was added to the reaction solution at 0° C. After reacting at room temperature for 1 hour, the raw materials were completely reacted, the solvent was dried by rotary evaporation, the residue was dissolved with ethyl acetate, and washed with water for 3 times, then washed with saturated brine, and dried over anhydrous sodium sulfate, and then dried by rotary evaporation to obtain Compound 11-1.

The Compound 11-1 was dissolved in DMF, and sodium azide (1.5 eq) was added to the solution, then the reaction was carried out in an oil bath at 90° C. for 5 hours. The raw materials were completely reacted, DMF was concentrated, then the residue was diluted with ethyl acetate, and washed with water for 3 times, then washed with saturated brine, and dried over anhydrous sodium sulfate, and then dried by rotary evaporation to obtain Compound 11-2.

The Compound 11-2 was dissolved in acetonitrile, and 10% Pd/C (0.2 eq) was added to the solution. After reacting for 6 hours at room temperature under a hydrogen atmosphere, the raw materials were completely reacted. The mixture was suction filtered with diatomaceous earth, and the filtrate was dried by rotary evaporation, then Compound 11-3 was obtained by silica gel column chromatography (DCM:MeOH=40:1).

The Compound 11-3 was dissolved in dichloromethane, and DIPEA (1.5 eq) was added to the solution. Then methylsulfonyl chloride (1.2 eq) was added to the reaction solution at 0° C. After reacting at 0° C. for 1 hour, the raw materials were completely reacted. The reaction was quenched by adding saturated ammonium chloride, then dichloromethane and water were added for extraction. The organic layer was washed with saturated brine, dried over anhydrous sodium sulfate, dried by rotary evaporation, then Compound 11-4 was obtained by silica gel column chromatography (DCM:MeOH=80:1).

The Compound 11-4 was dissolved in dichloromethane, and 4M HCl in dioxane was added to the reaction solution. After 30 minutes, the solvent was dried by rotary evaporation to obtain Compound 11-5.

Reference was made to the Example of synthesis of Compound S1, Compound S11 was obtained by using Compound 11-5 as the raw material. $^1$H NMR (400 MHz, Methanol-$d_4$) δ 8.38 (d, J=1.5 Hz, 1H), 7.24 (dt, J=19.5, 2.4 Hz, 4H), 6.17 (d, J=8.9 Hz, 1H), 5.59 (s, 1H), 4.72 (q, J=9.0 Hz, 1H), 4.57 (t, J=4.5 Hz, 1H), 4.40 (dd, J=9.8, 7.5 Hz, 1H), 4.23 (dd, J=9.8, 7.3 Hz, 1H), 3.91-3.74 (m, 2H), 3.37 (d, J=1.4 Hz, 3H), 3.21 (s, 1H), 3.03-2.84 (m, 2H), 2.59 (q, J=5.8, 5.2 Hz, 1H), 2.43 (dd, J=14.2, 8.1 Hz, 1H), 2.37-2.25 (m, 2H). MS(ESI): [M+H]$^+$ m/z 533.6

Preparation of Compound S12

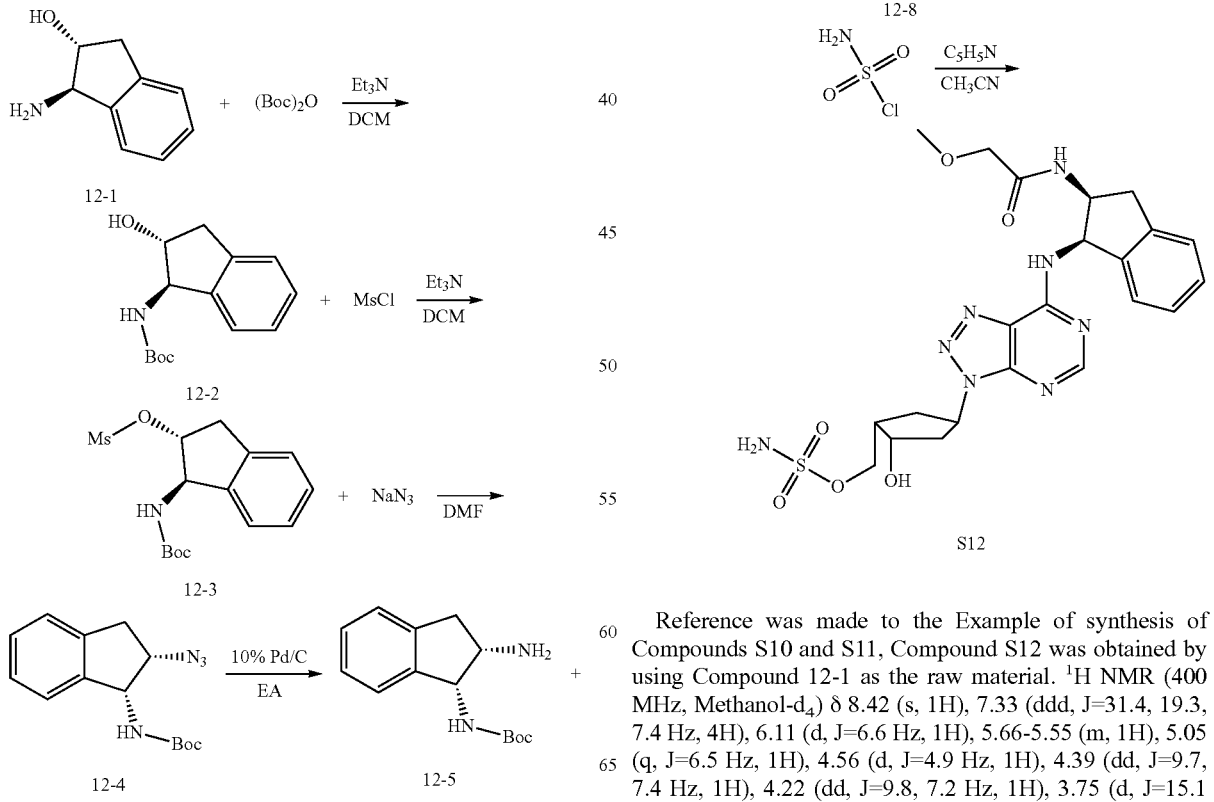

Reference was made to the Example of synthesis of Compounds S10 and S11, Compound S12 was obtained by using Compound 12-1 as the raw material. $^1$H NMR (400 MHz, Methanol-$d_4$) δ 8.42 (s, 1H), 7.33 (ddd, J=31.4, 19.3, 7.4 Hz, 4H), 6.11 (d, J=6.6 Hz, 1H), 5.66-5.55 (m, 1H), 5.05 (q, J=6.5 Hz, 1H), 4.56 (d, J=4.9 Hz, 1H), 4.39 (dd, J=9.7, 7.4 Hz, 1H), 4.22 (dd, J=9.8, 7.2 Hz, 1H), 3.75 (d, J=15.1 Hz, 1H), 3.64 (d, J=15.1 Hz, 1H), 3.36 (d, J=7.6 Hz, 5H), 3.21-3.12 (m, 1H), 2.88 (s, 1H), 2.64-2.52 (m, 1H), 2.49-2.38 (m, 1H), 2.38-2.23 (m, 2H). MS(ESI): [M+H]⁺ m/z 533.6
Preparation of Compound S13
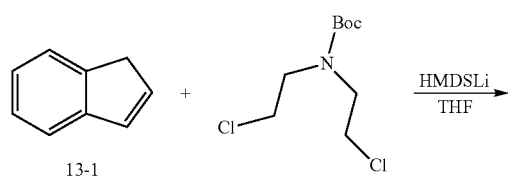
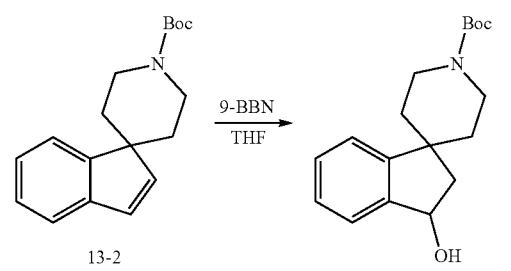
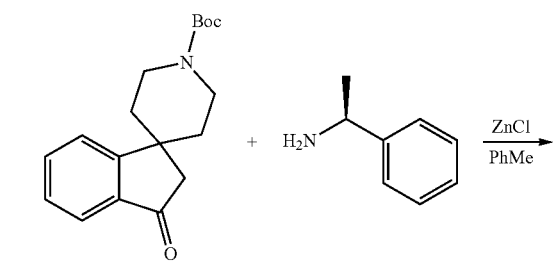
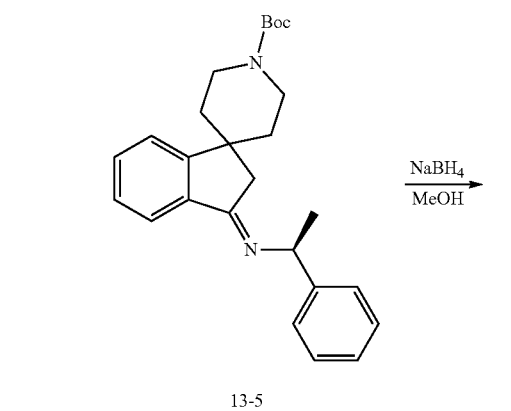

-continued

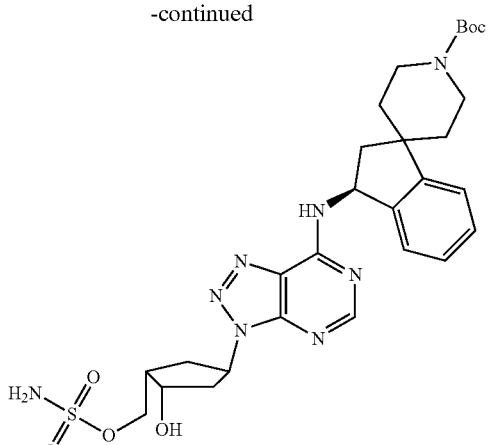

S13

Under the protection of argon, the Compound 13-1 was dissolved in THF, and HMDLi (2 eq) was added dropwise to the solution at 0° C., then reacted at 0° C. for 1 hour. Then tert-butyl N, N-bis(2-chloroethyl)carbamate (1 eq) was diluted with THF, and added dropwise to the reaction flask and the reaction was continued for 2 hours. The raw materials were completely reacted. The reaction was quenched with saturated ammonium chloride, and the reaction solution was concentrated, dissolved with ethyl acetate, and water was added for extraction. The organic layer was washed with saturated brine, dried over anhydrous sodium sulfate, dried by rotary evaporation, then Compound 13-2 was obtained by silica gel column chromatography (PE:EA=40:1).

The Compound 13-2 was dissolved in THF, and 9-BBN (3 eq) was added to the solution. After reacting at 70° C. for 3 hours, the raw materials were completely reacted. The reaction solution was cooled to 0° C., and 3 M NaOH solution (1.2 eq) and 30% hydrogen peroxide solution (1.2 eq) were added to the reaction solution, and reacted at room temperature for 1 hour. Then the reaction solution was concentrated, diluted with ethyl acetate, and water was added for extraction. The organic layer was washed with saturated brine, dried over anhydrous sodium sulfate, and dried by rotary evaporation to obtain Compound 13-3.

The Compound 13-3 was dissolved in dichloromethane, and PDC (2.1 eq) was added to the solution. After reacting for 10 hours at room temperature, the raw materials were completely reacted. The mixture was suction filtered with diatomaceous earth, and the filtrate was dried by rotary evaporation, then Compound 13-4 was obtained by silica gel column chromatography (PE:EA=8:1).

Under the protection of nitrogen, the Compound 13-4 was dissolved in anhydrous toluene by using a water separator, and S-phenethylamine (1.2 eq) and anhydrous zinc chloride (0.03 eq) were added to the solution, after the reaction was refluxed by condensation for 8 hours, the raw materials were completely reacted. The solvent was dried by rotary evaporation, and the residue was dissolved with ethyl acetate, washed in sequence with 0.1 M NaOH solution twice, saturated ammonium chloride once, saturated brine once, and dried over anhydrous sodium sulfate, and then dried by rotary evaporation to obtain Compound 13-5.

Under the protection of nitrogen, the Compound 13-5 was dissolved in anhydrous methanol, and sodium borohydride (1 eq) was added to the solution in batches at −40° C., then the reaction was slowly raised to 0° C. and continued for 2 hours. The raw materials were completely reacted, then the reaction was quenched with saturated ammonium chloride, and the reaction solution was concentrated, dissolved with ethyl acetate, and extracted with water. The organic layer was washed with saturated brine, dried over anhydrous sodium sulfate, and dried by rotary evaporation to obtain a crude product. The crude product was dissolved in ether, a 2 M HCl in ether was added to the solution until a large amount of solid was precipitated out, then filtered with suction to obtain Compound 13-6.

The Compound 13-6 was dissolved in methanol, and 10% Pd/C (0.2 eq) and ammonium formate (20 eq) were added to the reaction. After reacting for 24 hours at 60° C., the raw materials were completely reacted. The mixture was suction filtered with diatomaceous earth, and the filtrate was dried by rotary evaporation, and the residue was dissolved with ethyl acetate. The organic layer was washed with saturated brine, then washed with saturated brine, and dried over anhydrous sodium sulfate, dried by rotary evaporation, then Compound 13-7 was obtained by silica gel column chromatography (DCM:MeOH=10:1).

Reference was made to the Example of synthesis of Compound S1, Compound S13 was obtained by using Compound 13-7 as the raw material. $^1$H NMR (400 MHz, Methanol-$d_4$) δ 8.42-8.35 (m, 1H), 7.27 (ddd, J=16.2, 9.9, 6.8 Hz, 4H), 6.06 (t, J=7.9 Hz, 1H), 5.60 (d, J=8.1 Hz, 1H), 4.57 (s, 1H), 4.40 (dd, J=9.8, 7.4 Hz, 1H), 4.23 (dd, J=9.8, 7.3 Hz, 1H), 4.11 (d, J=13.6 Hz, 2H), 3.15-2.85 (m, 4H), 2.59 (q, J=7.1, 5.9 Hz, 1H), 2.44 (dd, J=14.1, 8.1 Hz, 1H), 2.38-2.25 (m, 2H), 2.09 (tt, J=12.4, 6.1 Hz, 1H), 1.97 (dd, J=13.0, 8.2 Hz, 1H), 1.73-1.56 (m, 3H), 1.49 (s, 9H). MS(ESI): [M+H]$^+$ m/z 615.4

Preparation of Compound S14

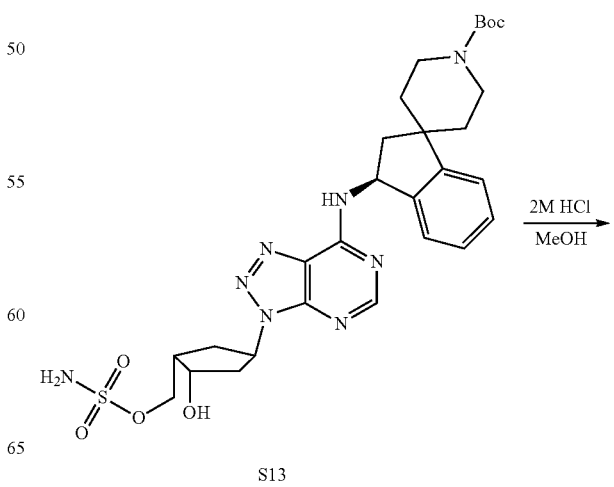

S13

41

-continued

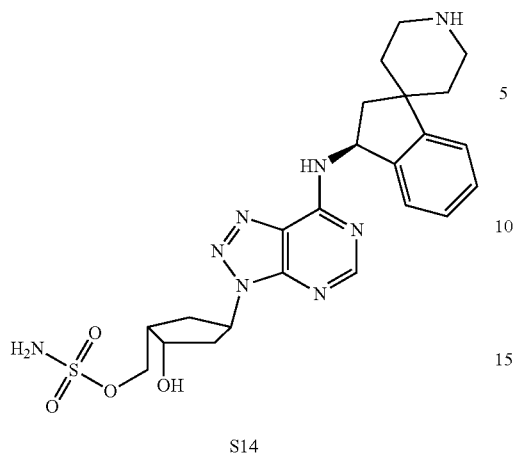

S14

The Compound S13 was dissolved in methanol, 2 M HCl methanol solution was added to the reaction solution, and the reaction was stirred at room temperature for 5 hours. The raw materials were completely reacted. The solvent was dried by rotary evaporation, and the mixture was extracted with ethyl acetate and saturated sodium bicarbonate. The organic layer was washed with saturated brine, dried over anhydrous sodium sulfate, and dried by rotary evaporation, then Compound S14 was obtained by silica gel column chromatography (DCM:MeOH=20:1). $^1$H NMR (400 MHz, Methanol-$d_4$) δ 8.40 (s, 1H), 7.35-7.29 (m, 2H), 7.29-7.17 (m, 2H), 6.04 (t, J=7.9 Hz, 1H), 5.61 (dt, J=8.1, 4.0 Hz, 1H), 4.57 (dt, J=4.6, 2.4 Hz, 1H), 4.40 (dd, J=9.8, 7.5 Hz, 1H), 4.23 (dd, J=9.8, 7.3 Hz, 1H), 3.07 (d, J=12.9 Hz, 2H), 2.92 (qd, J=9.8, 7.8, 3.1 Hz, 3H), 2.80 (td, J=12.7, 2.7 Hz, 1H), 2.61 (ddd, J=14.0, 7.5, 4.5 Hz, 1H), 2.45 (ddd, J=14.1, 8.2, 1.9 Hz, 1H), 2.32 (ddd, J=9.7, 6.8, 3.6 Hz, 2H), 2.17 (td, J=13.0, 4.2 Hz, 1H), 1.99-1.87 (m, 1H), 1.82-1.56 (m, 3H). MS(ESI): [M+H]$^+$ m/z 515.6

Preparation of Compound S15

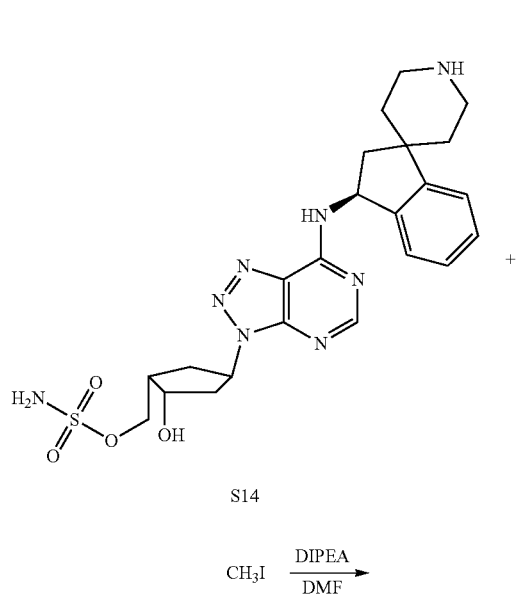

S14

$\xrightarrow{\text{CH}_3\text{I}}{\text{DIPEA}/\text{DMF}}$

42

-continued

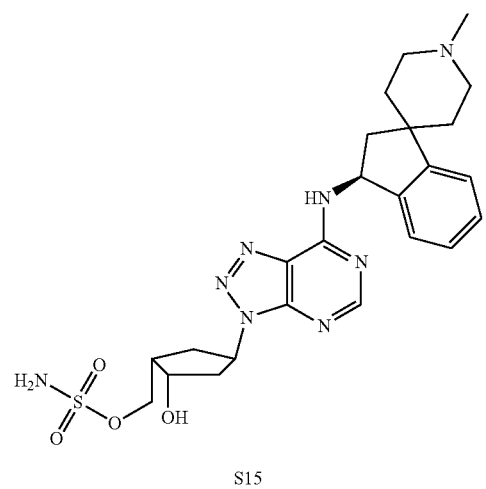

S15

The Compound S14 was dissolved in DMF, and DIPEA (2 eq) and methyl iodide (1.05 eq) were added to the solution, and the reaction was stirred at room temperature for 20 minutes. The raw materials reacted completely, DMF was concentrated, then the residue was diluted with ethyl acetate, and washed in sequence with water and saturated brine, and dried over anhydrous sodium sulfate, and then dried by rotary evaporation to obtain Compound S15. $^1$H NMR (400 MHz, Methanol-$d_4$) δ 8.40 (s, 1H), 7.32 (d, J=4.0 Hz, 2H), 7.29-7.19 (m, 2H), 6.03 (t, J=7.9 Hz, 1H), 5.66-5.56 (m, 1H), 4.57 (td, J=4.5, 1.9 Hz, 1H), 4.40 (dd, J=9.8, 7.4 Hz, 1H), 4.23 (dd, J=9.8, 7.3 Hz, 1H), 2.88 (ddd, J=26.1, 12.6, 8.6 Hz, 4H), 2.61 (ddd, J=13.9, 7.5, 4.6 Hz, 1H), 2.45 (ddd, J=14.0, 8.1, 1.8 Hz, 1H), 2.39-2.20 (m, 8H), 1.88 (ddd, J=26.8, 13.3, 8.8 Hz, 2H), 1.76-1.59 (m, 2H). MS(ESI): [M+H]$^+$ m/z 529.6

Preparation of Compound S16

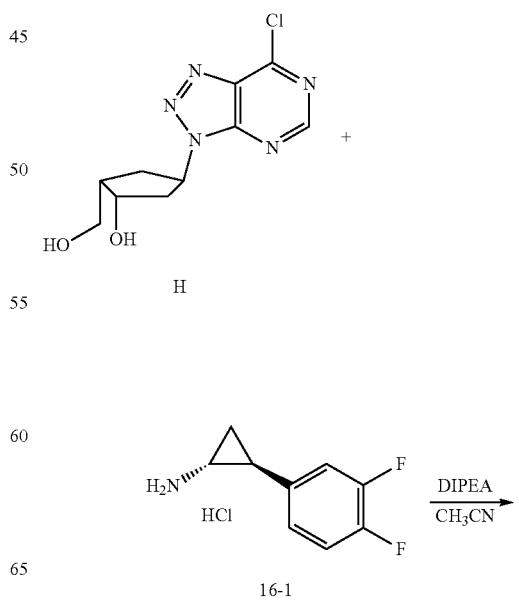

16-1

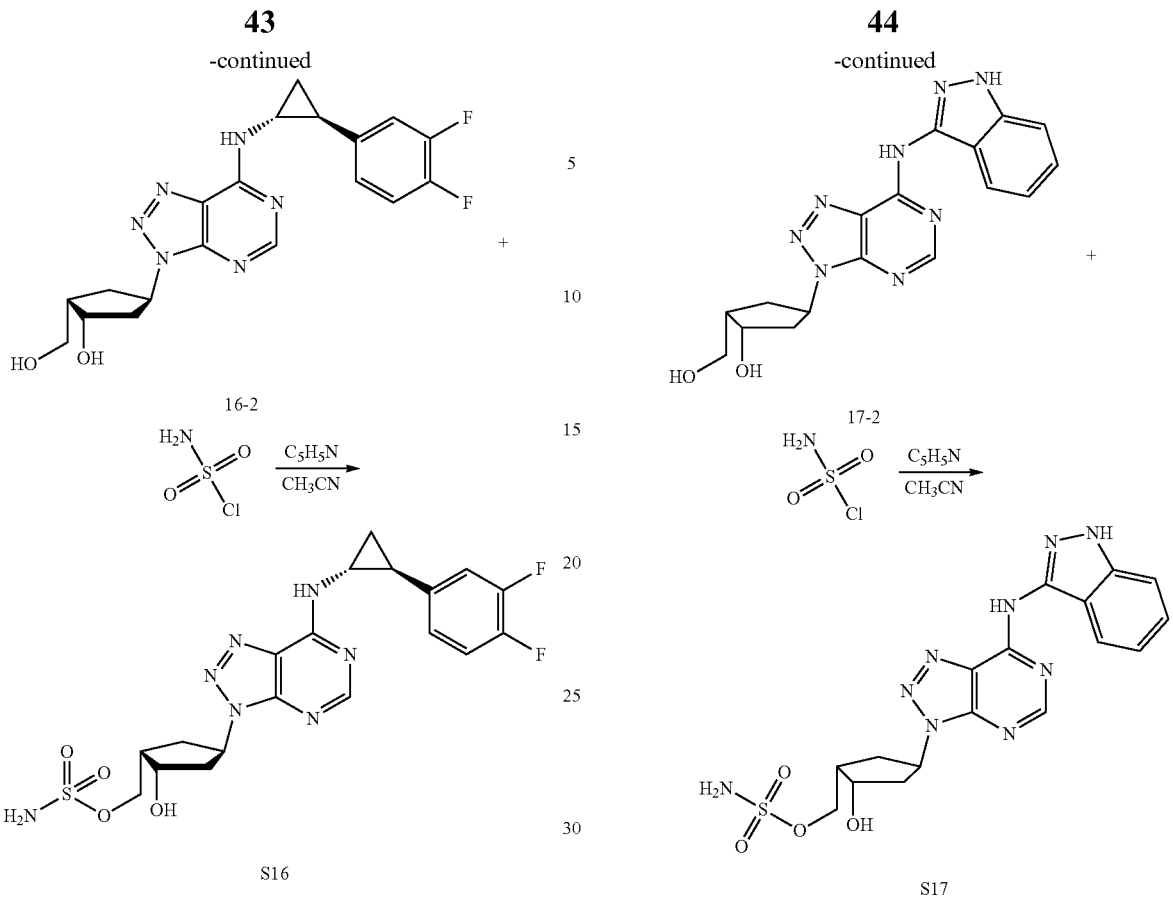

Reference was made to the Example of synthesis of Compound S1, Compound S16 was obtained by using Compound 16-1 as the raw material. $^1$H NMR (400 MHz, Methanol-$d_4$) δ 8.42 (s, 1H), 7.25-7.01 (m, 3H), 5.66-5.56 (m, 1H), 4.58 (t, J=4.5 Hz, 1H), 4.41 (dd, J=9.8, 7.5 Hz, 1H), 4.24 (dd, J=9.7, 7.3 Hz, 1H), 3.21 (dt, J=8.0, 3.9 Hz, 1H), 2.92 (s, 1H), 2.62 (ddd, J=12.7, 7.5, 4.8 Hz, 1H), 2.45 (dd, J=14.1, 8.2 Hz, 1H), 2.36-2.19 (m, 3H), 1.51-1.36 (m, 2H). MS(ESI): [M+Na]$^+$ m/z 504.2

Reference was made to the Example of synthesis of Compound S1, Compound S17 was obtained by using Compound 17-1 as the raw material. $^1$H NMR (400 MHz, Methanol-$d_4$) δ 9.00-8.93 (m, 1H), 7.63 (d, J=7.2 Hz, 1H), 7.39 (d, J=9.3 Hz, 1H), 7.26 (t, J=7.9 Hz, 1H), 6.72 (s, 1H), 5.82 (s, 1H), 4.62 (s, 1H), 4.42 (dd, J=9.8, 7.4 Hz, 1H), 4.29-4.20 (m, 1H), 2.98 (s, 1H), 2.75-2.64 (m, 1H), 2.58-2.48 (m, 1H), 2.41 (dd, J=10.7, 7.6 Hz, 2H). MS(ESI): [M+H]$^+$ m/z 446.4

Preparation of Compound S17

Preparation of Compound S18

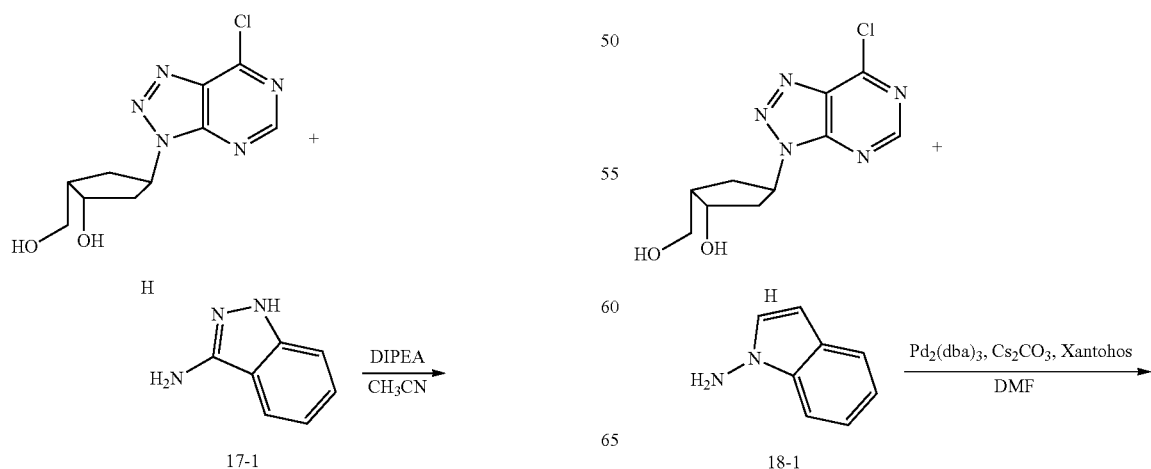

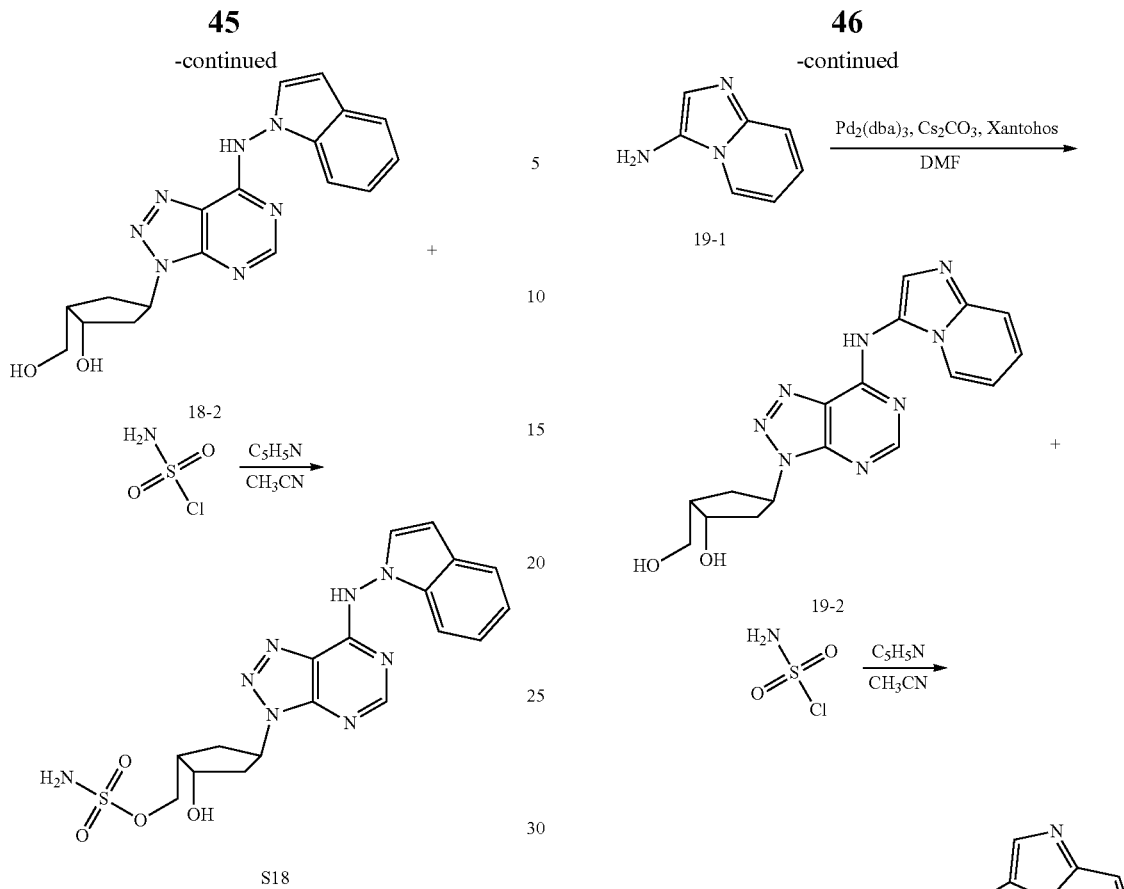

Under the protection of nitrogen, the Compound H was dissolved in DMF, and a Compound 18-1 (1.5 eq), Pd$_2$(dba)$_3$ (0.1 eq), Cs$_2$CO$_3$ (2.5 eq), Xantohos (0.3 eq) were added to the solution. The mixture was stirred at room temperature for 4 hours, and the raw materials were completely reacted. The mixture was filtered with suction, and the filtrate was dried by rotary evaporation, then a Compound 18-2 was obtained by silica gel column chromatography (DCM: MeOH=20:1). Reference was made to the Example of synthesis of Compound S1, Compound S18 was obtained by using Compound 18-2 as the raw material. $^1$H NMR (400 MHz, Methanol-d$_4$) δ 8.33 (s, 1H), 7.64-7.59 (m, 1H), 7.31 (d, J=3.4 Hz, 1H), 7.22 (d, J=7.9 Hz, 1H), 7.13 (dtd, J=18.1, 7.1, 1.3 Hz, 2H), 6.61 (d, J=3.4 Hz, 1H), 5.66 (s, 1H), 4.57 (s, 1H), 4.40 (dd, J=9.8, 7.5 Hz, 1H), 4.23 (dd, J=9.7, 7.2 Hz, 1H), 2.92 (s, 1H), 2.61 (s, 1H), 2.53-2.41 (m, 1H), 2.33 (s, 2H). MS(ESI): [M+Na]$^+$ m/z 467.3

Preparation of Compound S19

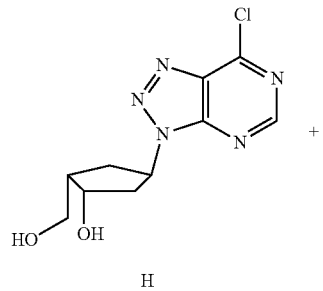

Reference was made to the Example of synthesis of Compound S18, Compound S19 was obtained by using Compound 19-1 as the raw material. $^1$H NMR (400 MHz, Methanol-d$_4$) δ 8.36 (s, 1H), 8.21-8.11 (m, 1H), 7.79-7.62 (m, 2H), 7.48 (t, J=8.0 Hz, 1H), 7.03 (t, J=6.9 Hz, 1H), 5.66 (s, 1H), 4.58 (s, 1H), 4.40 (dd, J=9.8, 7.4 Hz, 1H), 4.23 (dd, J=9.8, 7.3 Hz, 1H), 2.92 (s, 1H), 2.61 (s, 1H), 2.46 (s, 1H), 2.34 (t, J=8.7 Hz, 2H). MS(ESI): [M+H]$^+$ m/z 446.4

Preparation of Compound S20

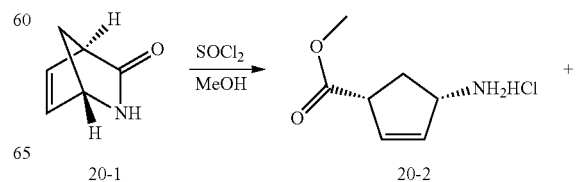

47

-continued

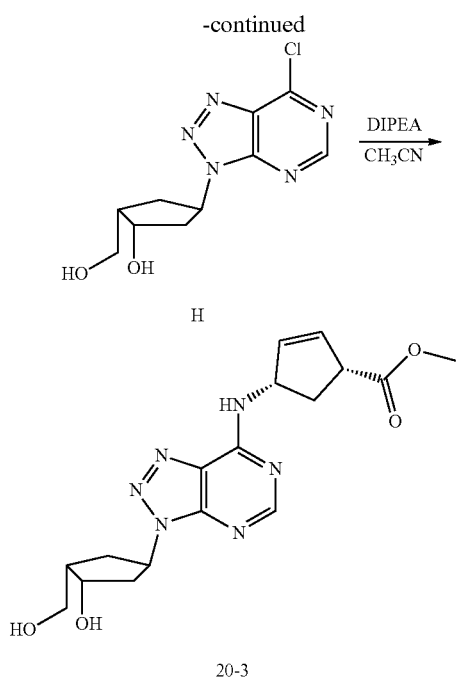

48

Preparation of Compound S21

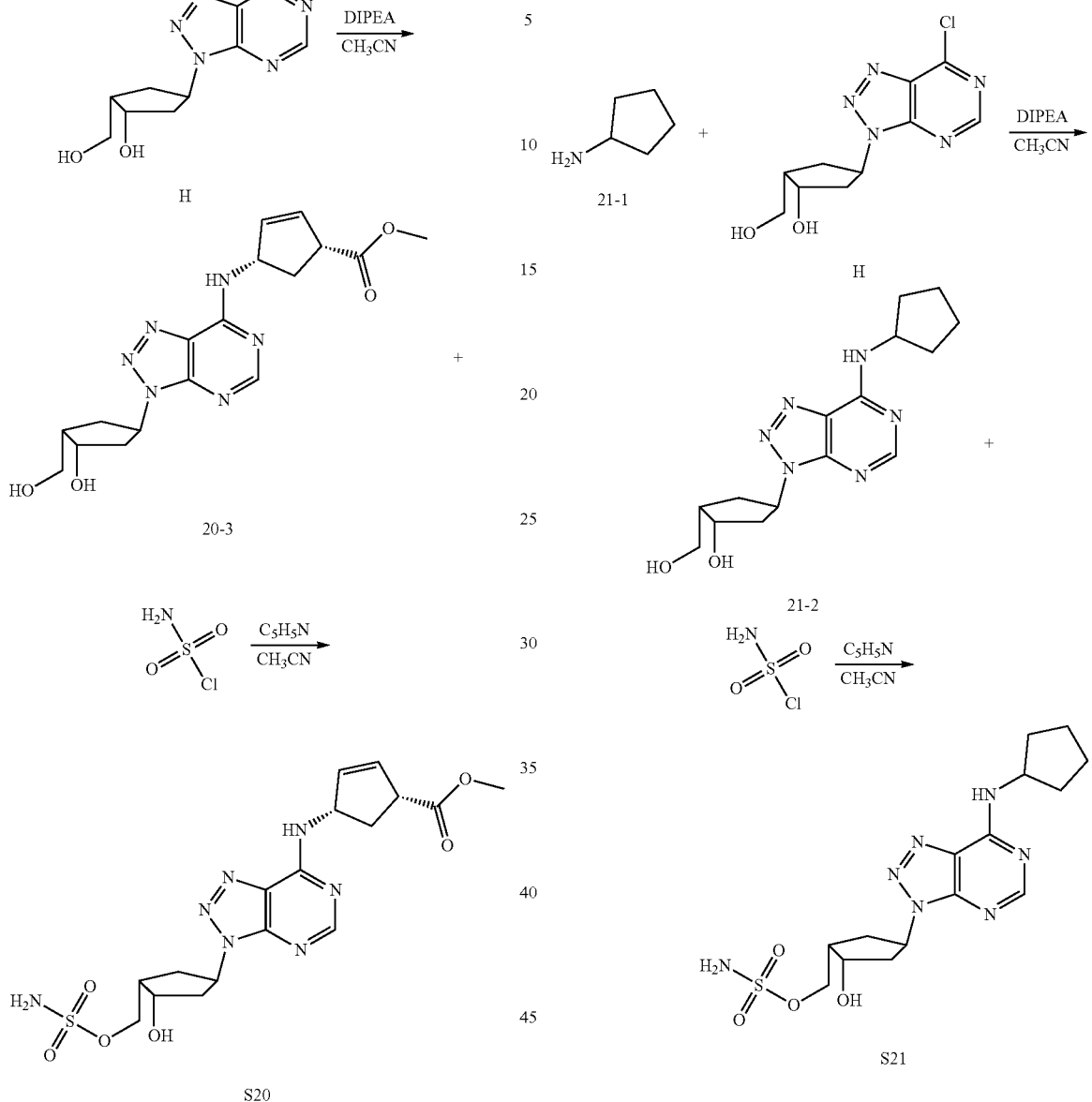

The Compound 20-1 was dissolved in methanol, and thionyl chloride (2.2 eq) was added to the solution. The reaction was stirred at 0° C. for 2 hours, and the raw materials were completely reacted. Then the solvent was dried by rotary evaporation to obtain Compound 20-2.

Reference was made to the Example of synthesis of Compound S1, Compound S20 was obtained by using Compound 20-2 as the raw material. $^1$H NMR (400 MHz, Methanol-$d_4$) δ 8.37 (s, 1H), 6.09-5.95 (m, 2H), 5.64-5.55 (m, 1H), 5.46 (ddd, J=8.2, 5.8, 2.0 Hz, 1H), 4.57 (td, J=4.6, 1.9 Hz, 1H), 4.40 (dd, J=9.7, 7.4 Hz, 1H), 4.22 (dd, J=9.8, 7.3 Hz, 1H), 3.73 (s, 3H), 3.68 (tt, J=6.2, 2.7 Hz, 1H), 2.89 (s, 1H), 2.75 (dt, J=13.7, 8.5 Hz, 1H), 2.60 (ddd, J=14.0, 7.5, 4.6 Hz, 1H), 2.43 (ddd, J=14.0, 8.1, 1.8 Hz, 1H), 2.31 (ddd, J=9.5, 6.9, 3.3 Hz, 2H), 2.13-2.04 (m, 1H). MS(ESI): [M+H]$^+$ m/z 454.4

Reference was made to the Example of synthesis of Compound S1, Compound S21 was obtained by using Compound 21-1 as the raw material. $^1$H NMR (400 MHz, Methanol-$d_4$) δ 8.33 (s, 1H), 5.58 (qd, J=8.0, 4.9 Hz, 1H), 4.64-4.53 (m, 2H), 4.40 (dd, J=9.8, 7.4 Hz, 1H), 4.22 (dd, J=9.8, 7.3 Hz, 1H), 2.95-2.83 (m, 1H), 2.59 (ddd, J=13.9, 7.4, 4.7 Hz, 1H), 2.43 (ddd, J=14.0, 8.2, 1.9 Hz, 1H), 2.30 (ddd, J=9.7, 6.8, 3.8 Hz, 2H), 2.11 (s, 2H), 1.83 (h, J=4.3, 3.8 Hz, 2H), 1.68 (tq, J=11.9, 7.9, 6.2 Hz, 4H). MS(ESI): [M+H]$^+$ m/z 398.4

Biological Evaluation

The present disclosure was further described and explained hereafter in combination with Test Examples, but these examples are not meant to limit the scope of the present disclosure.

Experimental Example: The Test of Inhibiting NAE Enzyme Activity at the Molecular Level by Some Compounds in Examples 1. Preliminary Evaluation Experiment of Inhibiting NAE Enzyme Activity at the Molecular Level by Compounds Homogeneous Time-Resolved Fluorescence (HTRF) technology was used to detect the in vitro inhibitory effect of the compound on NAE enzyme activity. The experimental operation steps were as follows:

(1) the enzyme reaction buffer was prepared using: 50 mM HEPES (pH 7.5), 0.05% BSA, 5 mM $MgCl_2$, 20 μM ATP, 250 μM L-glutathione;

(2) a NAE enzyme (human recombinant APPBP1/UBA3) was prepared to 4 nM, and the substrate was prepared to a mixture containing 600 nM His6-NEDD8 and 320 nM GST-UBE2M/Ubc12;

(3) the test compound was diluted to 40 μM, and then a 10 times gradient dilution was performed;

(4) 10 μL of reaction system was prepared in a 384-well plate, and 5 μL of NAE enzyme, 2.5 μL of mixed substrate and 2.5 μL of test compound were added. The final reaction system included: 2 nM NAE enzyme, 150 nM His6-NEDD8, 80 nM GST-UBE2M/Ubc12 and 10 μM starting test compound. Two repeated wells per group were set up, and a negative control without enzyme and an enzyme group control were additionally set up;

(5) the plate was incubated on a shaker at 27° C. for 2 h, then added 10 μL of stop solution: 0.1 M HEPES (pH 7.5), 0.05% Tween 20, 20 mM EDTA, 410 mM KF, Anti-6HIS-Eu Cryptate (CisBio, 1:200), Anti-GST-XL665 (CisBio, 1:200);

(6) the plate was left at room temperature overnight, then the plate was read with a fluorescence enzyme-labeled instrument (PE Envision) with excitation light source of Lance and absorption wavelength of 620 nm/665 nm.

(7) the inhibition rate of the compound was calculated by the following formula:

a. Reading processing: (665/620)*10000 mean value–mean value of negative control group b.

$$\text{Inhibition rate (\%)} = \left(1 - \frac{\text{mean value of compound group}}{\text{mean value of enzyme control group}}\right) \times 100$$

C. $IC_{50}$ was calculated with a GraphPad software.

2. Preliminary Evaluation Experiment of Inhibiting NAE Enzyme Activity at the Molecular Level by Compounds

TABLE 2

Inhibitory effects of some compounds in Examples on NAE enzyme activity

| Compound | IR (10 μM) | $IC_{50}$* (nM) | Compound | IR (10 μM) | $IC_{50}$* (nM) |
|---|---|---|---|---|---|
| S1 | 99.0% | A | S2 | 99.5% | A |
| S3 | 98.8% | A | S4 | 98.6% | A |
| S5 | 95.2% | B | S6 | 95.8% | A |
| S7 | 96.1% | B | S8 | 98.3% | A |
| S9 | 98.3% | A | S10 | 98.3% | A |
| S11 | 0.84% | C | S12 | 85.0% | B |
| S13 | 96.0% | A | S14 | 91.4% | A |
| S15 | 77.0% | B | S16 | 85.2% | C |
| S17 | 7.9% | C | S18 | 43.3% | C |
| S19 | 57.8% | C | S20 | 84.8% | A |
| S21 | 48.2% | C | MLN4924 | 98.6% | A |

*A indicates $IC_{50}$ < 100 nM, B indicates 100 nM ≤ $IC_{50}$ < 1 μM, C indicates $IC_{50}$ ≥ 1 μM.

Experimental Example: Inhibitory Effects of Some Compounds in Examples on Proliferation Activity of HCT-116 Cell The inhibitory effects of the compounds on the proliferation of human colon cancer cells HCT-116 were detected by a sulforodamine B (SRB) method. The specific steps were as follows: HCT-116 cells in the logarithmic phase were seeded into a 96-well culture plate at a suitable density with 90 μL per well. After overnight cultivation, the compounds at different concentrations were added to act for 72 h, and a solvent control group (negative control) was set. After 72 h of the compounds acting on the cells, the effects of the compounds on cell proliferation were detected using the SRB method as follows. The culture solution was discarded, and 100 μL/well of 10% trichloroacetic acid (TCA) pre-cooled at 4° C. was added, fixed at 4° C. for 1 h, then washed with distilled water for 5 times, and naturally dried in the air; 100 μL/well of SRB (4 mg/ml) solution prepared by 1% glacial acetic acid was added, stained at room temperature for 15 minutes; the supernatant was removed, washed with 1% acetic acid for 5 times, and air dried; 150 μl/well of Tris (10 mM) solution was added, then left at room temperature for 15 minutes; finally, a full-wavelength microplate enzyme-labeled instrument SpectraMax 190 was used to read with a measurement wavelength of 560 nm.

The inhibition rate (%) of the compound on tumor cell growth was calculated by the following formula:

Inhibition rate (%) =

(OD control well − OD administration well)/OD control well × 100%

TABLE 3 inhibitory effects of some compounds in Examples on proliferation of HCT-116 cells

| Compound | HCT-116 $IC_{50}$* (μM) | Compound | HCT-116 $IC_{50}$* (μM) |
|---|---|---|---|
| S1 | A | S2 | A |
| S3 | B | S4 | B |
| S5 | C | S6 | C |
| S7 | C | S8 | C |
| S9 | A | S10 | A |
| S11 | C | S12 | C |
| S13 | A | S14 | C |
| S15 | B | S16 | C |
| S17 | C | S18 | C |
| S19 | C | S20 | C |
| S21 | C | MLN4924 | A |

*A indicates $IC_{50}$ < 10 nM, B indicates 10 nM ≤ $IC_{50}$ < 100 μM, C indicates $IC_{50}$ ≥ 100 μM.

Each of the technical features of the above-mentioned embodiments may be combined arbitrarily. To simplify the description, not all the possible combinations of each of the technical features in the above embodiments are described. However, all of the combinations of these technical features should be considered as within the scope of this disclosure, as long as such combinations do not contradict with each other.

The above-mentioned embodiments are merely illustrative of several embodiments of the present disclosure, which are described specifically and in detail, but it cannot be understood to limit the scope of the present disclosure. It should be noted that, for those ordinary skilled in the art, several variations and improvements may be made without departing from the concept of the present disclosure, and all of which are within the protection scope of the present disclosure. Therefore, the protection scope of the present disclosure shall be defined by the appended claims.

The invention claimed is:

1. A triazolopyrimidine having a structure represented by a formula (II):

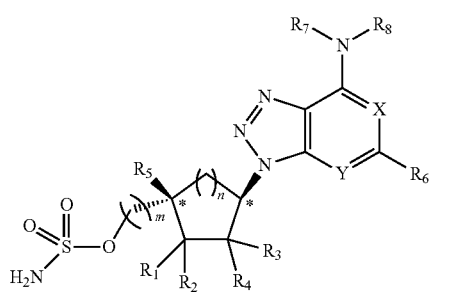

(II)

wherein, each of X and Y is N;
$R_1$ is hydroxy, and $R_2$, $R_3$, and $R_4$ are H;
$R_6$ is selected from the group consisting of: H, substituted or unsubstituted alkyl, substituted or unsubstituted alkoxy group, substituted or unsubstituted cycloalkyl, substituted or unsubstituted heterocyclyl, substituted or unsubstituted aryl, substituted or unsubstituted heteroaryl, silicyl, ketone group, carboxyl, ester group, alkoxycarbonyl, aryloxycarbonyl, amino group, cyano group, carbamoyl, haloformyl, isocyano-group, isocyanate group, thiocyanate group, isothiocyanate group, hydroxyl, nitro group and halogen;
$R_5$ is selected from the group consisting of: H, substituted or unsubstituted alkyl, substituted or unsubstituted alkoxy group, substituted or unsubstituted cycloalkyl, substituted or unsubstituted heterocyclyl, substituted or unsubstituted aryl, substituted or unsubstituted heteroaryl, silicyl, ketone group, carboxyl, ester group, alkoxycarbonyl, aryloxycarbonyl, amino group, cyano group, carbamoyl, haloformyl, isocyano-group, isocyanate group, thiocyanate group, isothiocyanate group, nitro group and halogen;
$R_7$ and $R_8$ are each independently selected from the group consisting of: H, substituted or unsubstituted linear alkyl, substituted or unsubstituted branched alkyl, substituted or unsubstituted cycloalkyl, substituted or unsubstituted heterocyclyl, substituted or unsubstituted aryl, and substituted or unsubstituted heteroaryl;
$R_7$ and $R_8$, together with a nitrogen atom to which the $R_7$ and $R_8$ are connected, can optionally form a three-to eight-membered heterocyclyl or a five-to ten-membered heteroaryl;
m is an integer of 1 to 20; and
n is 1, 2, 3, or 4.

2. The triazolopyrimidine compound of claim 1, wherein the triazolopyrimidine compound has a structure represented by a formula (III):

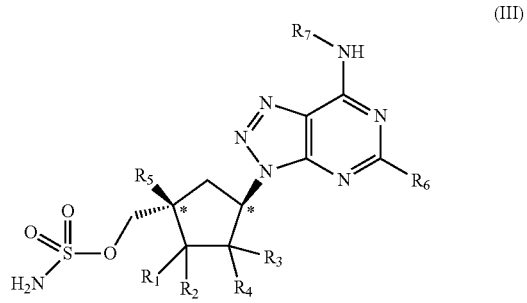

(III)

wherein, $R_1$ is hydroxy, and $R_2$, $R_3$, and $R_4$ are H;
$R_6$ is selected from the group consisting of: hydrogen atom, hydroxyl, amino group, halogen, C1-C8 alkyl, three-to eight-membered cycloalkyl, amide and ester group; and
$R_5$ is selected from the group consisting of hydrogen atom, amino group and halogen.

3. The triazolopyrimidine compound of claim 2, wherein the triazolopyrimidine compound has a structure represented by a formula (IV):

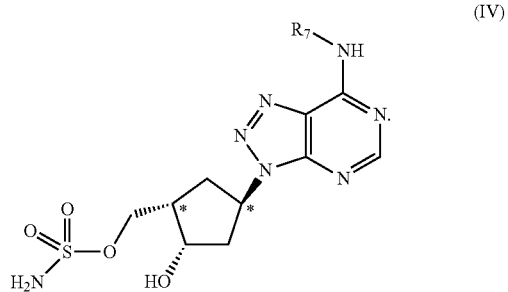

(IV)

4. The triazolopyrimidine compound of claim 1, wherein $R_7$ is selected from the group consisting of C1-C20 linear alkane, C1-C20 branched alkane, three-to ten-membered saturated cycloalkyl, three-to ten-membered unsaturated cycloalkyl, and substituents represented by the following structural formulas (V-1) to (V-4):

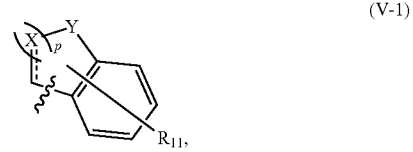

(V-1)

(V-2)

53

-continued

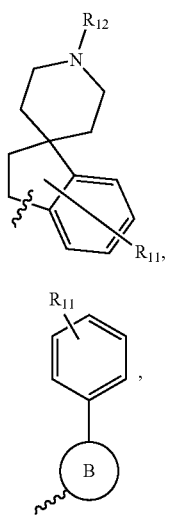
(V-3)

(V-4)

wherein, X and Y are each independently C or N;
⌇ represents a single bond or a double bond;
ring B is selected from the group consisting of: three-to eight-membered cycloalkane, benzene ring, thiophene ring, furan ring, pyrazole ring, imidazole ring, pyran ring, pyrrole ring, thiazole ring and oxazole ring;
p is 1 or 2;
q is 0, 1, 2, 3, 4, 5, 6, 7 or 8;
$R_{11}$ is selected from the group consisting of: H, substituted or unsubstituted alkyl, substituted or unsubstituted alkoxy, substituted or unsubstituted cycloalkyl, substituted or unsubstituted heterocyclyl, substituted or unsubstituted aryl, substituted or unsubstituted heteroaryl, silicyl, ketone group, ester group, amino group, alkoxycarbonyl, aryloxycarbonyl, cyano group, carbamoyl, haloformyl, isocyano-group, isocyanate group, thiocyanate group, isothiocyanate group, hydroxyl, nitro group and halogen; and
$R_{12}$ is selected from the group consisting of hydrogen atom, C1-C6 alkyl, alkoxycarbonyl, alkylaminocarbonyl, and aminocarbonyl.

5. The triazolopyrimidine compound of claim 4, wherein $R_7$ is selected from the group consisting of C1-C8 alkyl and the following groups:

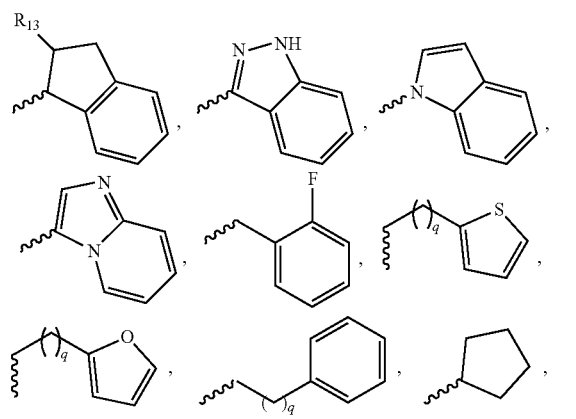

54

-continued

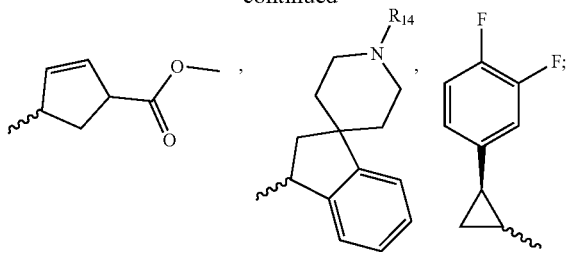

wherein, $R_{13}$ is selected from the group consisting of the following groups: hydrogen atom, hydroxyl, C1-C6 alkoxy group and

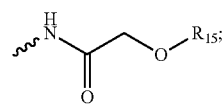

$R_{14}$ is selected from the group consisting of hydrogen atom, C1-C6 alkyl and -Boc;
$R_{15}$ is selected from the group consisting of hydrogen atom and C1-C6 alkyl; and
q is 0, 1, 2, 3, or 4.

6. The triazolopyrimidine compound of claim 1, wherein the triazolopyrimidine compound is optionally selected from compounds having the following structures:

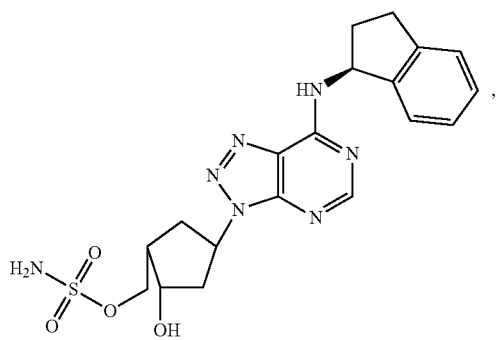

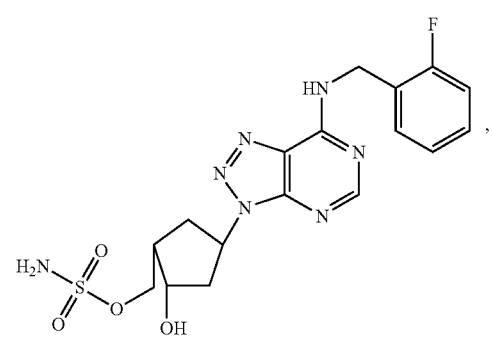

55
-continued
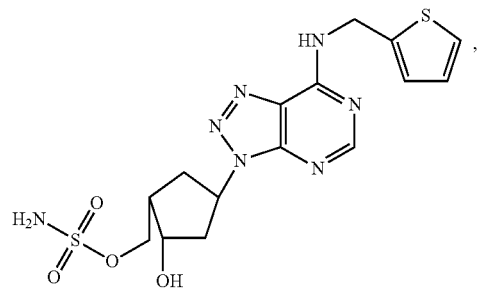
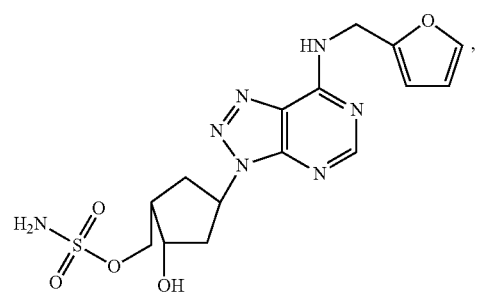
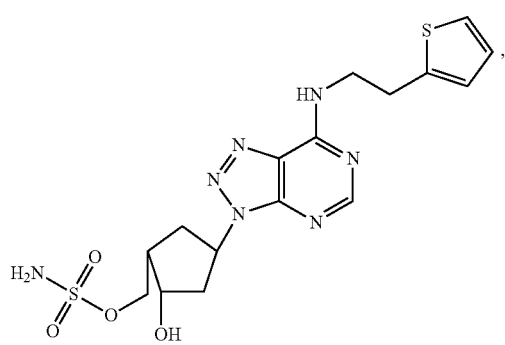
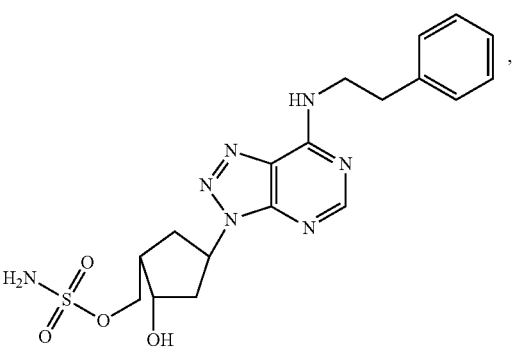
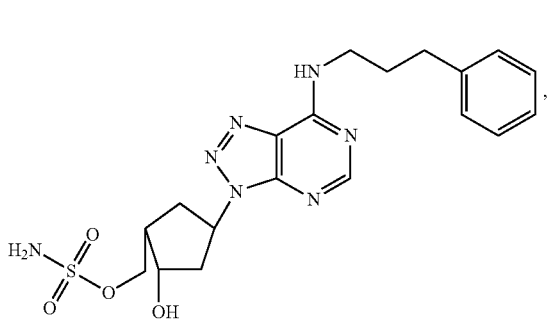
56
-continued
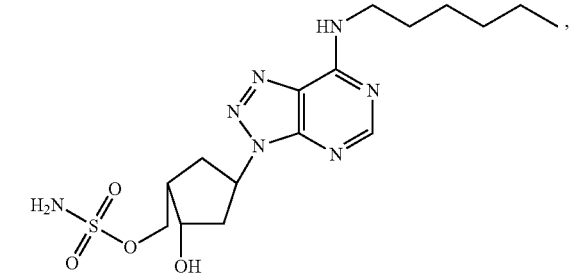
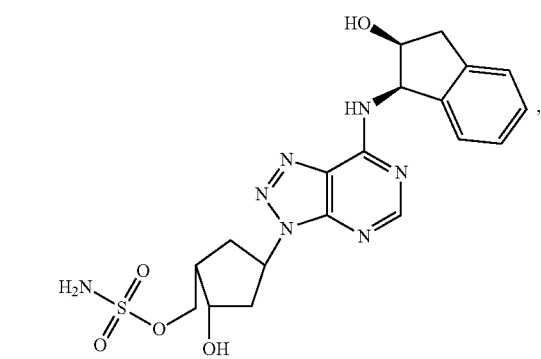
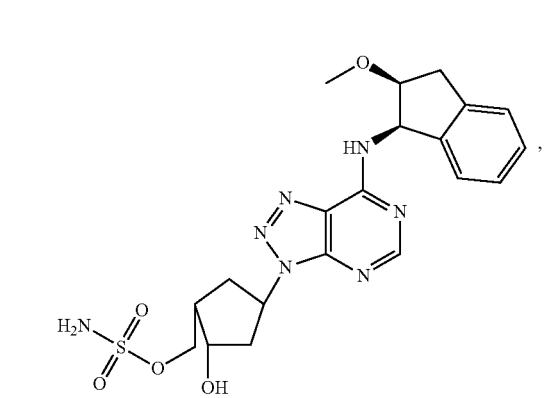
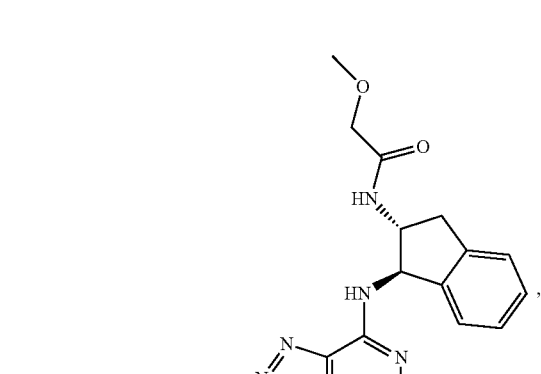
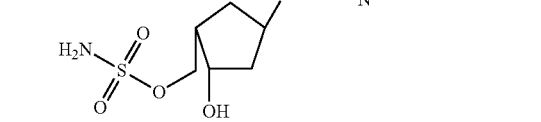

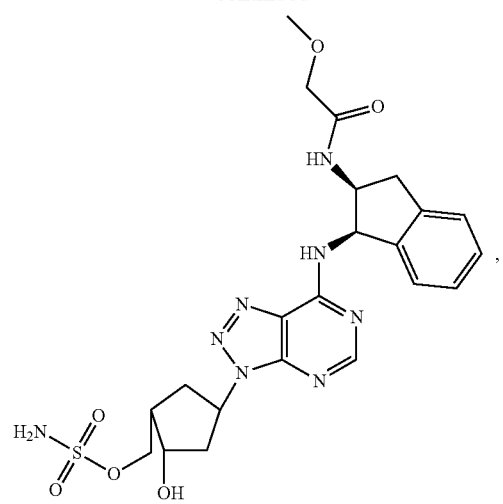
,
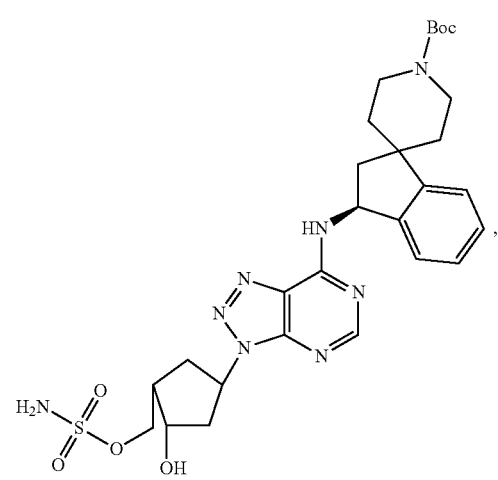
,
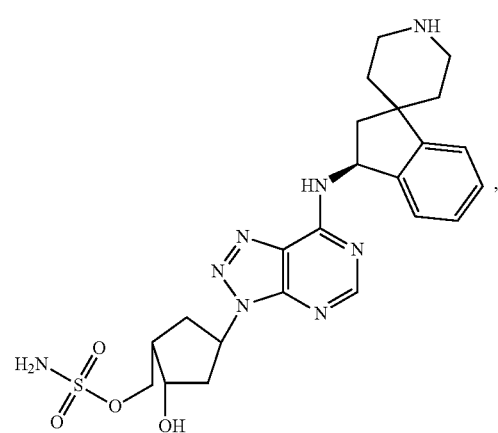
,
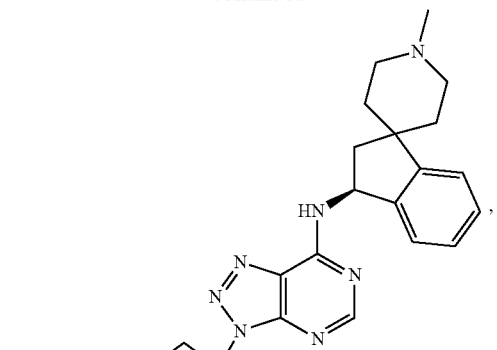
,
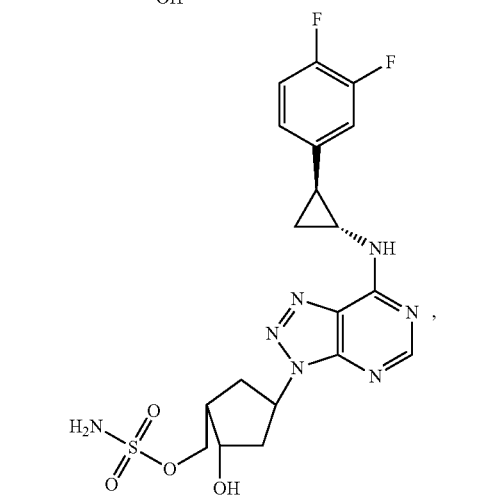
,
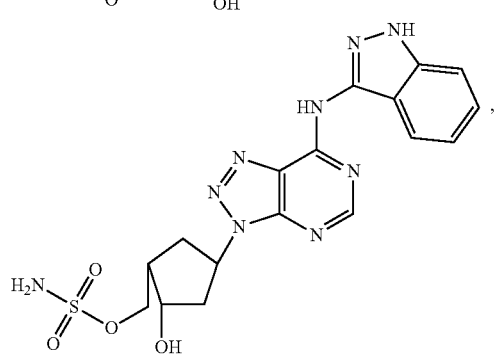
,
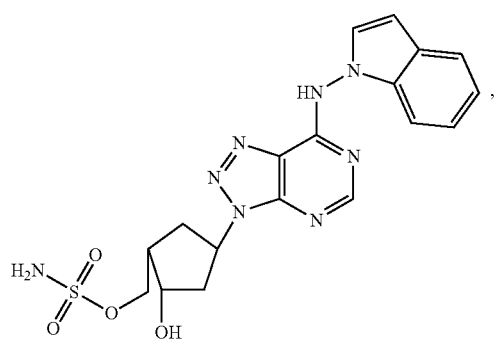
,

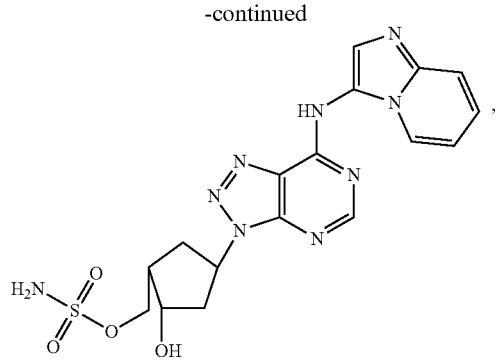

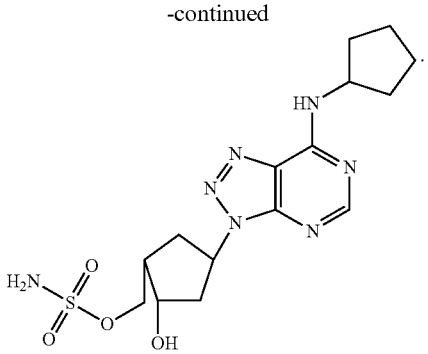

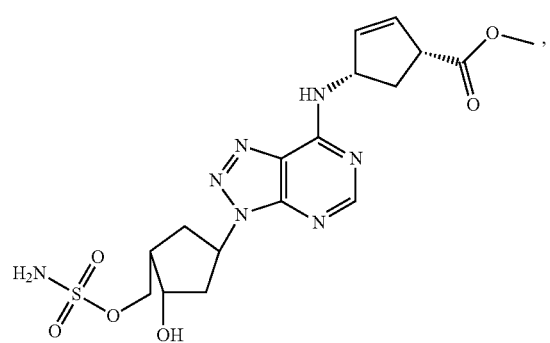

7. A pharmaceutically acceptable salt of the triazolopyrimidine compound of claim 1.

8. A composition comprising the triazolopyrimidine compound of claim 1.

9. A method of treating a cell proliferation disease or an E1 activating enzyme inhibition-related disease in a patient, the method comprising administering a pharmaceutical composition to the patient, wherein the pharmaceutical composition comprises the triazolopyrimidine compound of claim 1.

10. A method of treating a cell proliferation disease or an E1 activating enzyme inhibition-related disease in a patient, the method comprising administering a pharmaceutical composition to the patient, wherein the pharmaceutical composition comprises the pharmaceutically acceptable salt of claim 7.

* * * * *